(12) United States Patent
Tanaka et al.

(10) Patent No.: US 9,063,101 B2
(45) Date of Patent: Jun. 23, 2015

(54) CENTRALIZED MONITORING SYSTEM, ANALYZING SYSTEM AND CENTRALIZED MONITORING METHOD

(75) Inventors: Hiroyuki Tanaka, Kobe (JP); Hiroyoshi Nishio, Himeji (JP)

(73) Assignee: Sysmex Corporation, Hyogo (JP)

( * ) Notice: Subject to any disclaimer, the term of this patent is extended or adjusted under 35 U.S.C. 154(b) by 1087 days.

(21) Appl. No.: 13/052,909

(22) Filed: Mar. 21, 2011

(65) Prior Publication Data

US 2011/0223077 A1 Sep. 15, 2011

Related U.S. Application Data

(63) Continuation of application No. 11/715,958, filed on Mar. 9, 2007, now abandoned.

(30) Foreign Application Priority Data

Mar. 10, 2006 (JP) .................................. 2006-065927

(51) Int. Cl.
| | |
|---|---|
| *G01N 33/49* | (2006.01) |
| *G01N 35/00* | (2006.01) |

(Continued)

(52) U.S. Cl.
CPC .......... *G01N 35/00663* (2013.01); *G01N 33/49* (2013.01); *G01N 33/491* (2013.01); *G01F 23/56* (2013.01); *G01N 35/1002* (2013.01);

(Continued)

(58) Field of Classification Search
CPC .............................. G01N 33/49; G01N 33/491
USPC .................. 422/62, 67; 702/18, 22, 30, 31
See application file for complete search history.

(56) References Cited

U.S. PATENT DOCUMENTS

| | | | |
|---|---|---|---|
| 4,451,433 | A | 5/1984 | Yamashita et al. |
| 5,428,993 | A | 7/1995 | Kobashi |

(Continued)

FOREIGN PATENT DOCUMENTS

| | | |
|---|---|---|
| EP | 0052006 A1 | 5/1982 |
| EP | 0558212 A2 | 9/1993 |

(Continued)

OTHER PUBLICATIONS http://www.differencebetween.net/technology/difference-between-client-and-server/, downloaded Jun. 16, 2014.*

(Continued)

*Primary Examiner* — Jan Ludlow
(74) *Attorney, Agent, or Firm* — Sughrue Mion, PLLC

(57) ABSTRACT

An analyzing system, including: a plurality of inspection lines, each including a reagent supplying apparatus, and a plurality of hematology analyzers, each analyzing a measurement sample prepared from a blood sample and a reagent supplied from the reagent supplying apparatus; and a computer connected to the reagent supplying apparatuses, wherein each reagent supplying apparatus includes a storing part adapted to store a concentrated reagent, a detector adapted to detect a weight of or liquid level in the storing part, a first controller adapted to calculate a remaining amount of the concentrated reagent from an output of the detector and to transmit the calculated amount to the computer, and wherein the computer includes a display, and a second controller adapted to receive the amount data transmitted from the reagent supplying apparatuses, to generate display data integrating the plurality of received amount data and to show the display data on the display.

7 Claims, 17 Drawing Sheets

(51) Int. Cl.
  *G01F 23/56* (2006.01)
  *G01N 35/10* (2006.01)
(52) U.S. Cl.
  CPC ........... *G01N2035/00326* (2013.01); *G01N 2035/00217* (2013.01)

(56) References Cited

U.S. PATENT DOCUMENTS

| | | | |
|---|---|---|---|
| 5,646,046 A | 7/1997 | Fischer et al. | |
| 5,719,059 A | 2/1998 | Mimura et al. | |
| 5,800,056 A | 9/1998 | Suzuki et al. | |
| 2001/0031501 A1 | 10/2001 | Nomura et al. | |
| 2002/0042142 A1* | 4/2002 | Kawamura | 436/50 |
| 2004/0091396 A1 | 5/2004 | Nakamura et al. | |
| 2004/0141882 A1 | 7/2004 | Mimura et al. | |
| 2005/0054083 A1* | 3/2005 | Vuong et al. | 435/287.2 |
| 2010/0104478 A1 | 4/2010 | Kondou | |

FOREIGN PATENT DOCUMENTS

| | | |
|---|---|---|
| EP | 0753745 A2 | 1/1997 |
| EP | 1136817 A2 | 9/2001 |
| JP | 05-312618 A | 11/1993 |
| JP | 11-304799 A | 11/1999 |
| JP | 2002-090369 A | 3/2002 |
| JP | 2005-106669 A | 4/2005 |
| WO | 95/05590 A1 | 2/1995 |

OTHER PUBLICATIONS

Japanese Patent Office, "Office Communication," issued in connection with Japanese Patent Application No. 2006-065927.

\* cited by examiner

Fig. 10

| Date | Time | Inspection line | Reagent name | Message | Conductivity | The number of operations of pump | The number of re-tries |
|------|------|-----------------|--------------|---------|--------------|----------------------------------|------------------------|
| 08/10 | 12:57:10 | Line 4 | Concentrated reagent A | Preparation completes | 1114 | 14 | 0 |
| 08/10 | 12:57:05 | Line 2 | Concentrated reagent A | Preparation completes | 1114 | 14 | 0 |
| 08/10 | 12:57:01 | Line 3 | Concentrated reagent A | Preparation completes | 1114 | 14 | 0 |
| 08/10 | 12:56:10 | Line 4 | Concentrated reagent B | Preparation completes | 1113 | 13 | 2 |
| 08/10 | 12:56:05 | Line 2 | Concentrated reagent B | Preparation completes | 1113 | 13 | 2 |
| 08/10 | 12:56:01 | Line 3 | Concentrated reagent B | Preparation completes | 1113 | 13 | 2 |
| 08/10 | 12:55:50 | Line 1 | Concentrated reagent A | Preparation completes | 1113 | 13 | 2 |
| 08/10 | 11:03:10 | Line 4 | Concentrated reagent A | Preparation completes | 1000 | 0 | 0 |
| 08/10 | 11:03:05 | Line 2 | Concentrated reagent A | Preparation completes | 1000 | 0 | 0 |
| 08/10 | 11:03:02 | Line 3 | Concentrated reagent A | Preparation completes | 1000 | 0 | 0 |
| 08/10 | 11:03:01 | Line 5 | Concentrated reagent A | Preparation completes | 1000 | 0 | 0 |
| 08/10 | 11:02:50 | Line 1 | Concentrated reagent A | Preparation completes | 1000 | 0 | 0 |
| 08/02 | 14:30:13 | Line 1 | Concentrated reagent A | Preparation completes | 1024 | 24 | 2 |
| 08/01 | 13:43:02 | Line 1 | Concentrated reagent A | Preparation completes | 1000 | 1 | 2 |
| 07/31 | 13:44:02 | Line 1 | Concentrated reagent B | Preparation completes | 1001 | 29 | 2 |
| 07/30 | 13:45:02 | Line 1 | Concentrated reagent A | Preparation completes | 1029 | 20 | 2 |
| 07/29 | 17:58:20 | Line 1 | Concentrated reagent A | Preparation completes | 1020 | 2 | 1 |
| 07/28 | 17:57:20 | Line 1 | Concentrated reagent B | Preparation completes | 1002 | 22 | 2 |
| 07/26 | 17:48:20 | Line 1 | Concentrated reagent A | Preparation completes | 1122 | 21 | 1 |
| 07/26 | 16:39:21 | Line 1 | Concentrated reagent A | Preparation completes | 1121 | 12 | 1 |
| 07/26 | 16:37:21 | Line 1 | Concentrated reagent A | Preparation completes | 1043 | 43 | 2 |
| 07/26 | 16:37:21 | Line 1 | Concentrated reagent B | Preparation completes | 1041 | 41 | 2 |
| 07/26 | 16:15:21 | Line 1 | Concentrated reagent A | Preparation completes | 1019 | 19 | 1 |

*Fig. 11*

| | Date | Time | Inspection time | Reagent name | Contents |
|---|---|---|---|---|---|
| | 08/10 | 13:00:10 | Line 4 | Concentrated reagent A | Dilution discharge is impossible |
| | 08/10 | 13:00:05 | Line 2 | Concentrated reagent A | Dilution discharge is impossible |
| | 08/10 | 13:00:01 | Line 3 | Concentrated reagent A | Dilution discharge is impossible |
| | 08/10 | 12:59:50 | Line 1 | Concentrated reagent A | Abnormal high value concentration |
| | 08/10 | 12:59:10 | Line 4 | Concentrated reagent B | Suction of reagent is impossible |
| | 08/10 | 12:59:05 | Line 2 | Concentrated reagent B | Suction of reagent is impossible |
| | 08/10 | 12:59:01 | Line 1 | Concentrated reagent B | Abnormal high value concentration |
| | 08/10 | 12:58:50 | Line 4 | Concentrated reagent A | Suction of reagent is impossible |
| | 08/10 | 12:58:10 | Line 2 | Concentrated reagent A | Suction of reagent is impossible |
| | 08/10 | 12:58:05 | Line 3 | Concentrated reagent A | Suction of reagent is impossible |
| | 08/10 | 12:58:01 | Line 1 | Concentrated reagent A | Dilution discharge is impossible |
| | 08/10 | 11:02:50 | Line 4 | Concentrated reagent A | Suction of reagent is impossible |
| | 08/10 | 12:57:50 | Line 2 | Concentrated reagent A | Suction of reagent is impossible |
| | 08/10 | 12:57:10 | Line 3 | Concentrated reagent A | Suction of reagent is impossible |
| | 08/10 | 12:57:05 | Line 1 | Concentrated reagent A | Dilution discharge is impossible |
| | 08/10 | 12:57:01 | Line 4 | Concentrated reagent B | Pressure declines |
| | 08/10 | 12:56:50 | Line 2 | Concentrated reagent B | Pressure declines |
| | 08/10 | 12:56:10 | Line 3 | Concentrated reagent A | Pressure declines |
| | 08/10 | 12:56:05 | Line 1 | Concentrated reagent A | Pressure declines |
| | 08/10 | 12:56:01 | Line 4 | Concentrated reagent A | Pressure declines |
| | 08/10 | 12:55:50 | Line 2 | Concentrated reagent A | Pressure declines |
| | 08/10 | 11:03:10 | Line 3 | Concentrated reagent A | Pressure declines |
| | 08/10 | 11:03:05 | Line 3 | Concentrated reagent A | Pressure declines |
| | 08/10 | 11:03:02 | Line 5 | Concentrated reagent A | Suction of pure water is impossible |

Fig. 12

CENTRALIZED MONITORING SYSTEM, ANALYZING SYSTEM AND CENTRALIZED MONITORING METHOD

CROSS REFERENCE TO RELATED APPLICATIONS

This is a continuation of U.S. patent application Ser. No. 11/715,958 filed Mar. 9, 2007, which claims the benefit of Japanese Patent Application No. 2006-065927 filed Mar. 10, 2006. The disclosures of the prior applications are hereby incorporated in their entireties by reference.

FIELD OF THE INVENTION

The present invention relates to a centralized monitoring system, an analyzing system and a centralized monitoring method. Especially, the present invention relates to a centralized monitoring system, an analyzing system which comprise a reagent supplying apparatus for supplying a reagent to an analyzer for analyzing a measurement sample prepared from a sample and the reagent, and a centralized monitoring method.

BACKGROUND

Conventionally, in an inspection facility such as a large-scale inspection center, a plurality of analyzers for analyzing a sample such as blood and urine, and a plurality of reagent supplying apparatuses for supplying a reagent to each analyzer are provided. In such an inspection facility, the reagent is supplied to each analyzer from the reagent supplying apparatuses, and on the side of the analyzer, the supplied reagent and the sample are blended, and a measurement sample for analysis is thereby prepared and analyzed. Then, generally a monitor for confirming a remaining amount of the reagent is provided in each reagent supplying apparatus, and an operator confirms the remaining amount of the reagent displayed on the monitor of each reagent supplying apparatus and performs maintenance such as an exchange of the reagent.

Then, conventionally, U.S. Pat. No. 5,428,993 proposes a technique of detecting the remaining amount of the reagent in the reagent supplying apparatuses and displaying the remaining amount of the reagent thus detected on the monitor. A reagent container placed on a weight sensor is connected through the tube to an automatic analyzer disclosed in this U.S. Pat. No. 5,428,993, and the reagent used for analysis is supplied to the automatic analyzer through the tube from inside the reagent container. In addition, the weight sensor has a function of transmitting to the automatic analyzer total weight data of the reagent container in which the reagent is stored. Then, the automatic analyzer that receives the total weight data transmitted from the weight sensor displays, on the monitor of the reagent supplying apparatus the remaining amount of the reagent and a warning of shortage of reagent calculated from the total weight data.

However, in the aforementioned conventional inspection facility, the remaining amount of the reagent is displayed on the monitor of each reagent supplying apparatus, thus involving a problem that an operator must move to each reagent supplying apparatus to confirm the remaining amount of the reagent. In addition, in order to grasp the remaining amount of the reagent, in the whole inspection facility, the operator needs to move around all the reagent supplying apparatuses to confirm the remaining amount of the reagent in each reagent supplying apparatus and record it on paper, etc. Therefore, labor and time are required for confirming information regarding the remaining amount of the reagent used for each reagent supplying apparatus, thus making it difficult to efficiently monitor the information regarding the remaining amount of the reagent.

SUMMARY

A first aspect of the present invention is a centralized monitoring system, comprising: a plurality of reagent supplying apparatuses, each of the reagent supplying apparatuses comprising supplying means for supplying a reagent to an analyzer for analyzing a measurement sample prepared from a sample and the reagent, and transmitting means for transmitting information regarding remaining amount of the reagent; generation means for generating integrated information by integrating the each remaining amount of the reagent in the reagent supplying apparatuses based on the information regarding the remaining amount of the reagent transmitted by the transmitting means; and display means for displaying the each remaining amount of the reagent in the reagent supplying apparatuses based on the integrated information generated by the generation means.

A second aspect of the present invention is an analyzing system, comprising: an analyzer for analyzing a measurement sample prepared from a sample and a reagent; a plurality of reagent supplying apparatuses, each of the reagent supplying apparatuses comprising supplying means for supplying the reagent to the analyzer, and transmitting means for transmitting information regarding remaining amount of the reagent; generation means for generating integrated information by integrating the each remaining amount of the reagent in the reagent supplying apparatuses based on the information regarding the remaining amount of the reagent transmitted by the transmitting means; and display means for displaying the each remaining amount of the reagent in the reagent supplying apparatuses based on the integrated information generated by the generation means.

A third aspect of the present invention is a centralized monitoring method, comprising steps of: (a) collecting information regarding each remaining amount of a reagent in a plurality of reagent supplying apparatuses, each of the reagent supplying apparatuses being configured to supply the reagent to an analyzer for analyzing a measurement sample prepared from a sample and the reagent; and (b) displaying the each remaining amount of the reagent in the reagent supplying apparatuses based on the information collected by the step (a).

BRIEF DESCRIPTION OF THE DRAWINGS

FIG. 10 is a view showing a screen (preparation history screen) displayed on the display part of the client computer of the analyzing system according to one embodiment as shown in FIG. 1;

FIG. 11 is a view showing a screen (preparation error history screen) displayed on the display part of the client computer of the analyzing system according to one embodiment as shown in FIG. 1;

FIG. 12 is a view showing a screen (reagent feeding error history screen) displayed on the display part of the client computer of the analyzing system according to one embodiment as shown in FIG. 1;

DETAILED DESCRIPTION OF THE EMBODIMENT

Preferred embodiments of the present invention will be explained based on the drawings hereunder.

First, an analyzing system 1 according to one embodiment of the present invention will be explained with reference to FIG. 1 to FIG. 6.

Figure 1:
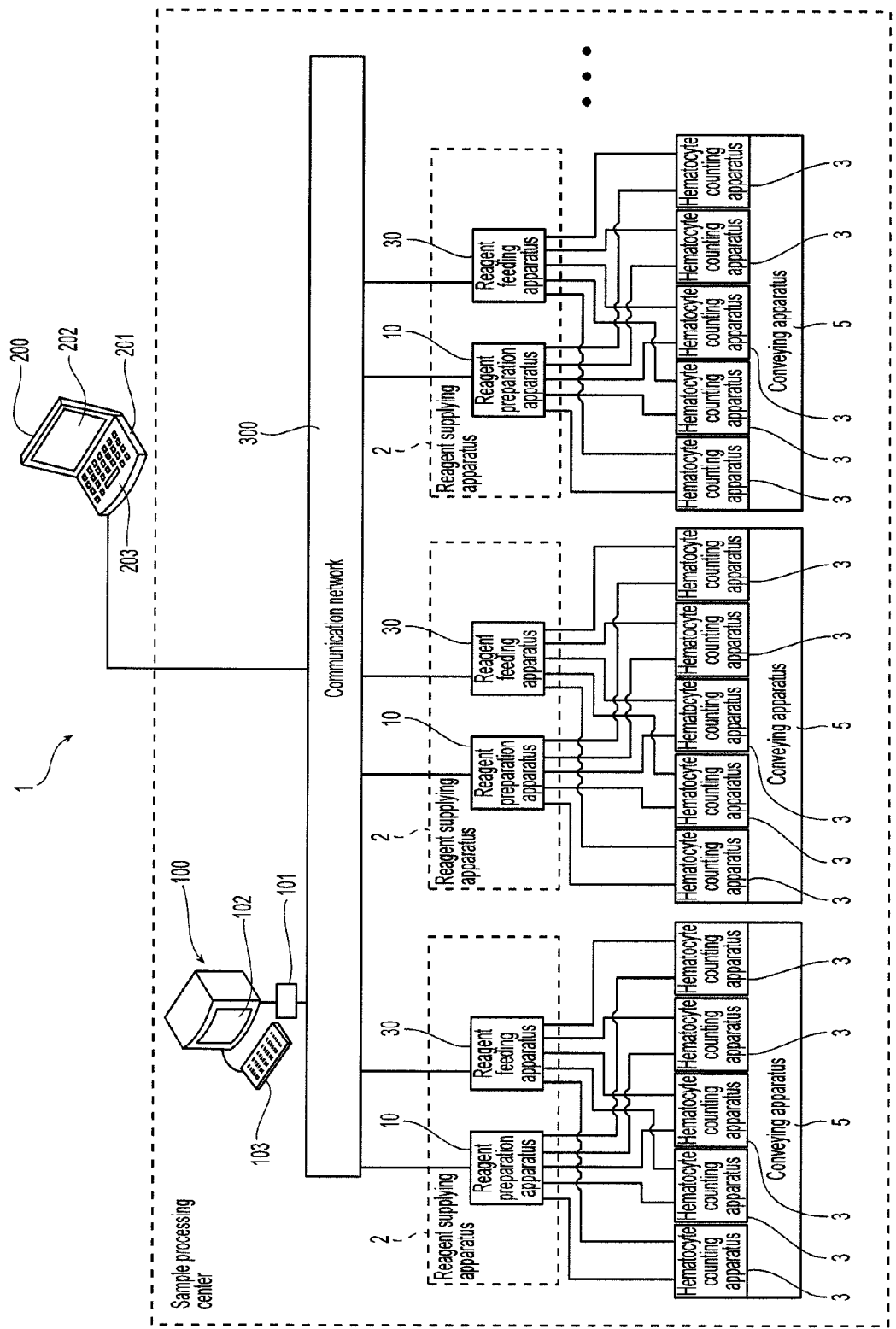
FIG. 1 is a schematic view showing a whole constitution of an analyzing system according to one embodiment of the present invention.

The analyzing system 1 according to one embodiment of the present invention is a system introduced to a facility where large numbers of samples (blood) are treated, such as an inspection room and an inspection center of a large scale hospital, and a constitution can be changed in accordance with a scale of an installed facility. In this analyzing system 1, as shown in FIG. 1, a server 100 in a sample processing center, a client computer 200 provided on a place separated from the sample processing center, and a plurality of reagent supplying apparatuses 2 are connected by a cable or radio through a communication network 300 such as a wire LAN and a wireless LAN, so as to communicate data with each other.

Figure 2:
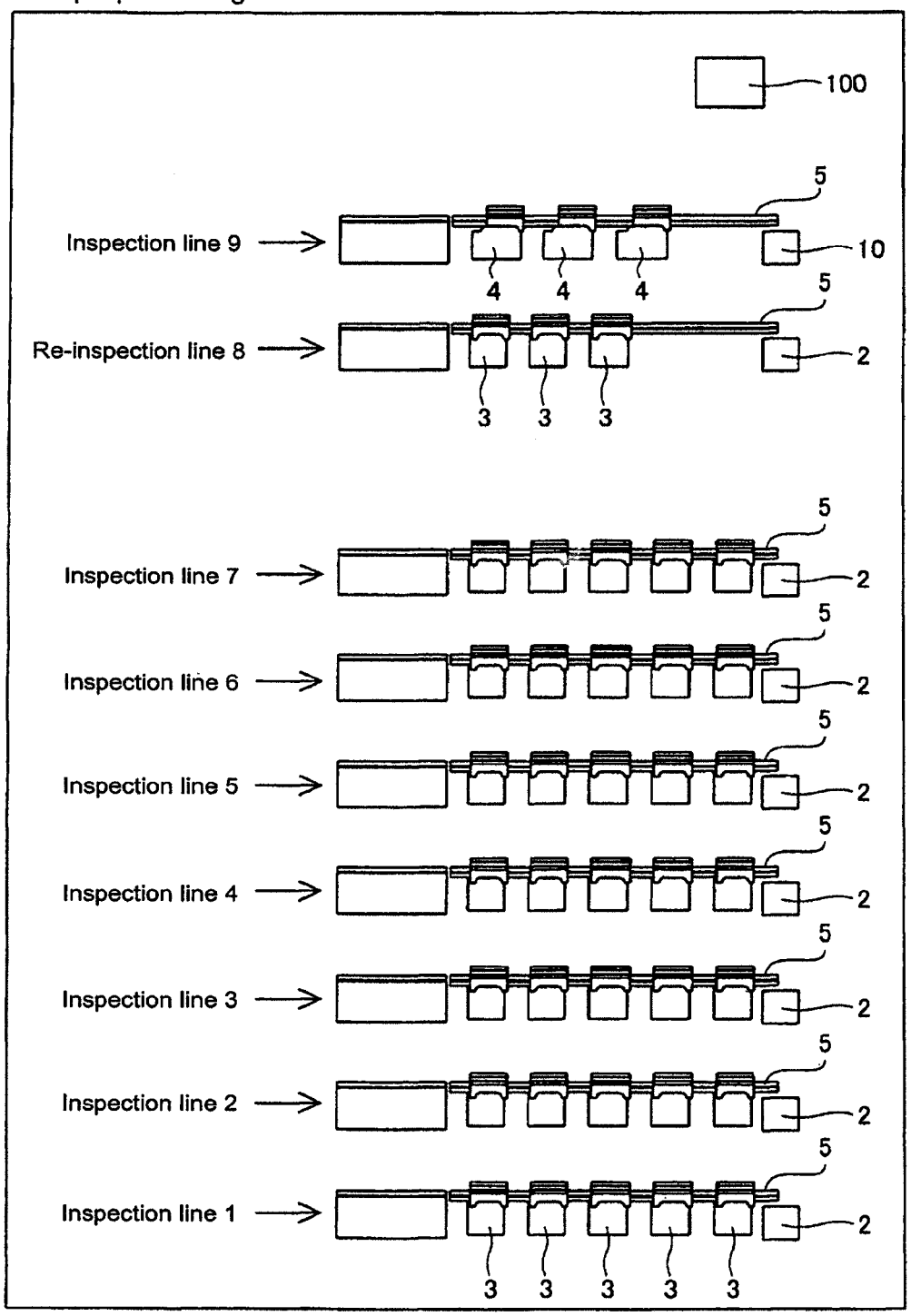
FIG. 2 is a schematic view showing an inspection line in an inspection center of the analyzing system according to one embodiment as shown in FIG. 1.

In the sample processing center, as shown in FIG. 2, inspection lines 1 to 7 for processing a plurality of collected samples and a re-inspection line 8 for processing the sample requiring re-inspection out of the samples inspected by the inspection lines 1 to 7 are provided in addition to the server 100 connected to the client computer 200. Each of the inspection lines 1 to 7 is composed of a reagent supplying apparatus 2 including a single reagent preparation apparatus 10 (see FIG. 1) and a single reagent feeding apparatus 30 (see FIG. 1); five hematocyte counting apparatuses 3 for analyzing a measurement sample for analysis prepared from the reagent (diluted solution and hemolytic agent) supplied from the reagent supplying apparatus 2 and the sample (blood); and a conveying apparatus 5 for conveying the sample to each hematocyte counting apparatus 3. Also, the re-inspection line 8 is composed of the aforementioned reagent supplying apparatus 2, three hematocyte counting apparatuses 3, and the conveying apparatus 5 for conveying the sample to each hematocyte counting apparatus 3. Note that the hematocyte counting apparatuses 3 function to calculate the number of red blood cells and the number of white blood cells in the blood. Further, separately from the inspection lines 1 to 7 and the re-inspection line 8, an inspection line 9 is provided, which is composed of a single reagent preparation apparatus 10, and three blood sample smearing apparatuses 4 for smearing a blood sample on a slide glass by using the diluted solution supplied from this reagent preparation apparatus 10. Note that in the blood sample smearing apparatus 4 of the inspection line 9, the reagent feeding apparatus 30 is not provided, unlike the inspection lines 1 to 7 and the re-inspection line 8.

Figure 3:
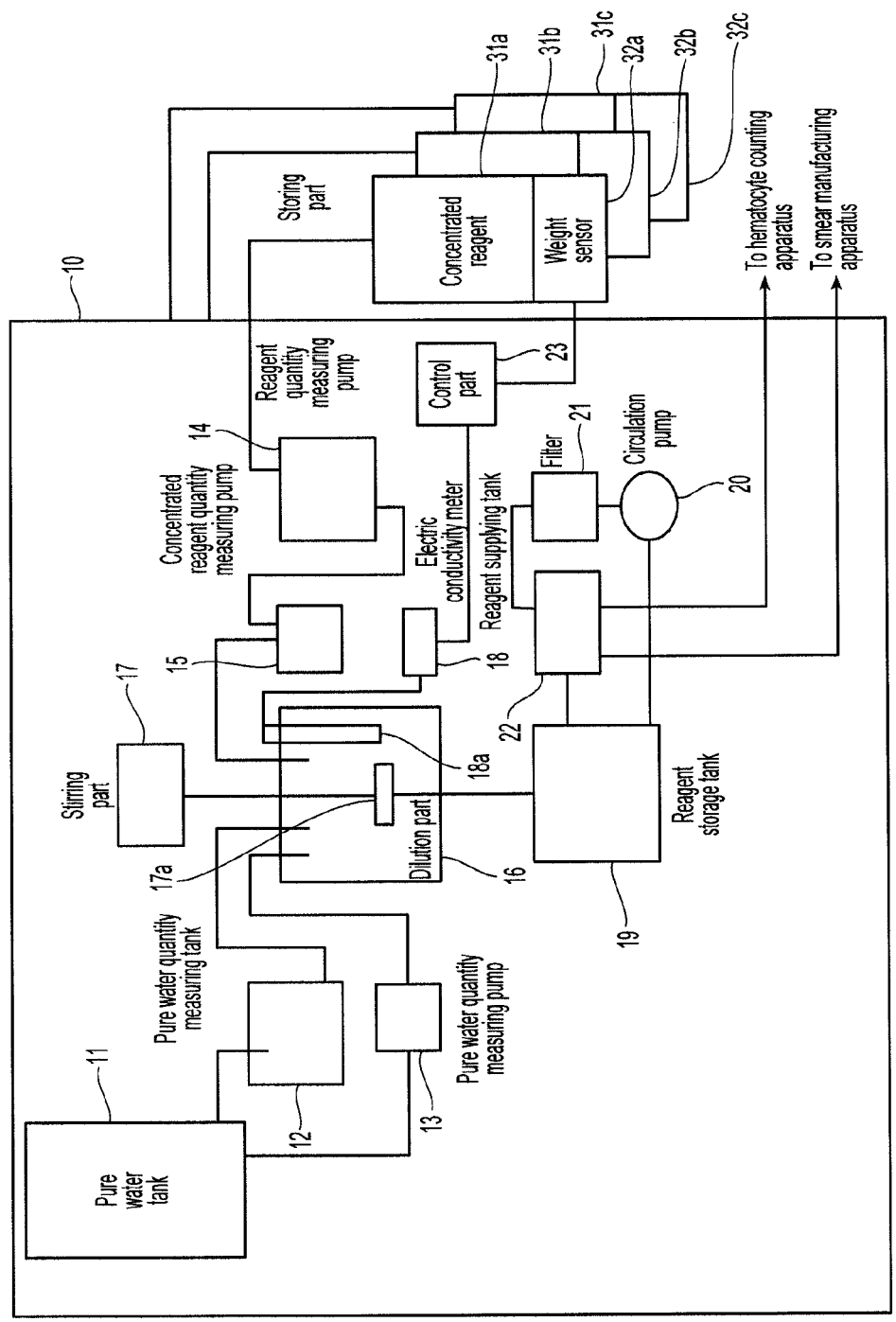
FIG. 3 is a block diagram of a reagent preparation apparatus of the analyzing system according to one embodiment as shown in FIG. 1.

The reagent preparation apparatus 10 provided in the inspection lines 1 to 7, the re-inspection line 8 and the inspection line 9 are provided for preparing the reagent (referred to as a diluted solution hereafter) by blending a concentrated saline solution for dilution (referred to as a concentrated reagent) and pure water, and thereafter supplying a diluted solution thus prepared to the hematocyte counting apparatuses 3 and the blood sample smearing apparatus 4. In this reagent preparation apparatus 10, as shown in FIG. 3, a pure water tank 11 for quantitatively measuring and supplying the pure water, a pure water quantity measuring tank 12, and a pure water quantity measuring pump (diaphragm pump) 13 are provided. In addition, in the reagent preparation apparatus 10, a reagent quantity measuring tank 14 and a concentrated reagent quantity measuring pump (diaphragm pump) 15 for quantitatively measuring and supplying the concentrated reagent are provided. Note that the concentrated reagent blended with the pure water by the reagent preparation apparatus 10 is stored in external storing parts 31a to 31c of the reagent preparation apparatus 10. In addition, the reagent preparation apparatus 10 includes a controller 23 that controls operations of a dilution part 16, a stirring part 17, an electric conductivity meter 18, a reagent storage tank 19, a circulation pump 20, a filter 21, a reagent supplying tank 22, and the reagent preparation apparatus 10. In addition, the reagent preparation apparatus 10 of this embodiment is connected to three storing parts 31a to 31c in which the concentrated reagent is respectively stored, and three sets of pure water quantity measuring tank 12, pure water quantity measuring pump 13, reagent quantity measuring tank 14, concentrated reagent quantity measuring pump 15, dilution part 16, stirring part 17, electric conductivity meter 18, reagent storage tank 19, circulation pump 20, filter 21, and reagent supplying tank 22, excluding the pure water tank 11 and the controller 23, are provided so as to correspond to the three storing parts 31a to 31c. Then, the pure water tank 11 and the controller 23 are shared by the aforementioned each part, three sets of which are provided as described above. Note that a concentrated reagent A is stored in the storing parts 31a and 31b respectively, and a concentrated reagent B is stored in the storing part 31c.

Also, in this embodiment, the storing parts 31a to 31c, in which the concentrated reagent is stored, are placed on weight sensors 32a to 32c having a function of detecting the weight of the storing parts 31a to 31c. In addition, the weight sensors 32a to 32c are connected to the controller 23, and detected weight data of the storing parts 31a to 31c is transmitted to the controller 23.

The pure water tank 11 is provided for storing the pure water supplied from outside the apparatus, and is connected to the pure water quantity measuring tank 12 and the pure water quantity measuring pump 13. Also, the pure water quantity measuring tank 12 has a function of sending the pure water stored in the pure water tank 11 to the dilution part 16, after quantitatively measuring the water. Further, the pure water quantity measuring pump (diaphragm pump) 13 has a function of discharging a fixed quantity of liquid, and discharges a fixed quantity of pure water from the pure water quantity measuring tank 12 to the dilution part 16.

The reagent quantity measuring tank 14 has a function of quantitatively measuring and storing the concentrated reagent stored in the external storing parts 31a to 31c. Also, the concentrated reagent quantity measuring pump (diaphragm pump) 15 has a function of discharging a fixed quantity of liquid, and discharges a fixed quantity of concentrated reagent from the reagent quantity measuring tank 14 to the dilution part 16.

The dilution part 16 is provided for receiving and blending the pure water and the concentrated reagent. In the inside the dilution part 16, a stirring wing 17a of the stirring part 17, and a detector 18a of the electric conductivity meter 18 are disposed. Also, the stirring part 17 has the stirring wing 17a for stirring the pure water and the concentrated reagent in the dilution part 16.

Further, in this embodiment, the electric conductivity meter 18 has the detector 18a that comes in contact with the dilution solution stored in the dilution part 16, and measures electric conductivity of the diluted solution in the dilution part 16. Then, the electric conductivity thus measured by the electric conductivity meter 18 is transmitted to the controller 23 which will be described later, and in the controller 23, whether or not measured electric conductivity is within a desired range is determined. Note that the electric conductivity is defined by an inverse number of an electric resistance of an electrolyte aqueous solution between electrodes filled with the electrolyte aqueous solution (diluted solution in this embodiment), and is an index showing a flowability of electricity flowing through the electrolyte aqueous solution. The electric conductivity is measured in this embodiment. This is because the electric conductivity changes depending on an amount (ion amount) of the concentrated reagent supplied to the dilution part 16, and therefore a change of the electric conductivity of a prepared diluted solution can be regarded as a change of a concentration of salts in the diluted solution. In addition, an electric conductivity value changes depending on a change of a temperature of the electrolyte aqueous solution, and therefore the temperature of the diluted solution is monitored by a temperature meter not shown. Then, the electric conductivity that fluctuates by temperature is corrected by the controller 23 which will be described later.

The reagent storage tank 19 is provided for receiving the diluted solution of a predetermined concentration (electric conductivity) in the dilution part 16. Accordingly, even when the concentrated reagent stored in the storing parts 31a to 31c runs out, a situation that the diluted solution is not supplied to the hematocyte counting apparatuses 3 (see FIG. 1 and FIG. 2) or the blood sample smearing apparatus 4 (see FIG. 2) from the reagent preparation apparatus 10 is prevented immediately, because a predetermined amount of diluted solution is stored in the reagent storage tank 19.

The circulation pump 20 is provided for circulating the diluted solution stored in the reagent storage tank 19 to the reagent supplying tank 22 and the reagent storage tank 19 through the filter 21. Then, the diluted solution passed through the filter 21 is partially stored in the reagent supplying tank 22, and is supplied to each hematocyte counting apparatus 3 (see FIG. 1 and FIG. 2) or the blood sample smearing apparatus 4 (see FIG. 2) from the reagent storage tank 19.

Here, in this embodiment, the controller 23 is connected to the weight sensors 32a to 32c on which the storing parts 31a to 31c storing the concentrated reagent are placed and the server 100, and has a function of receiving the weight data detected by the weight sensors 32a to 32c and transmitting it to the server 100. At this time, based on the weight data thus received, the controller 23 calculates the remaining amount (remaining amount data) of the concentrated reagent stored in the storing parts 31a to 31c, and thereafter transmits the calculated remaining amount data to the server 100.

Figure 4:
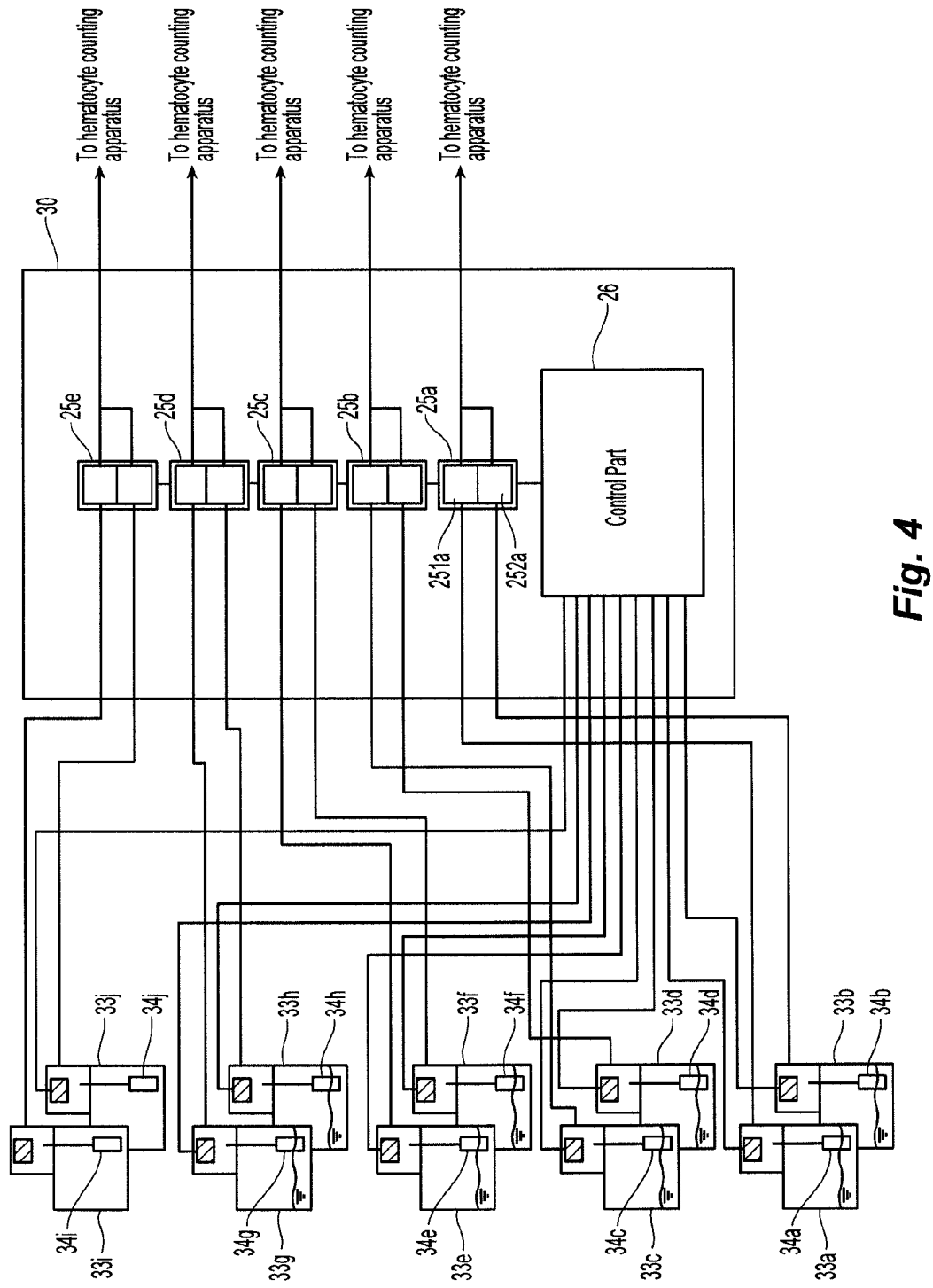
FIG. 4 is a block diagram of a reagent feeding apparatus of the analyzing system according to one embodiment as shown in FIG. 1.

Then, the reagent feeding apparatus 30 provided on the inspection lines 1 to 7 and the re-inspection line 8 are provided for supplying a hemolytic agent, whereby blood corpuscles in the blood is broken, to the hematocyte counting apparatuses 3. Accordingly, the reagent feeding apparatus 30 is not provided on the inspection line 9 where the hematocyte counting apparatuses 3 are not provided. As shown in FIG. 4, this reagent feeding apparatus 30 includes a switching valve 25a connected to a reagent tank 33a and a reagent tank 33b, a switching valve 25b connected to a reagent tank 33c and a reagent tank 33d, a switching valve 25c connected to a reagent tank 33e and a reagent tank 33f, a switching valve 25d connected to a reagent tank 33g and a reagent tank 33h, a switching valve 25e connected to a reagent tank 33i and a reagent tank 33j which are outside the apparatus, and a controller 26 for controlling an operation of the reagent feeding apparatus 30. Namely, the reagent feeding apparatus 30 of this embodiment is connected to 10 reagent tanks 33a to 33j. In addition, different kinds of hemolytic agents can be stored in the reagent tanks 33a and 33b, the reagent tanks 33c and 33d, the reagent tanks 33e and 33f, the reagent tanks 33g and 33h, and the reagent tanks 33i and 33j, respectively, and five kinds of the hemolytic agents in total can be set.

Further, in this embodiment, the switching valves 25a to 25e are controlled by the controller 26, and have a function of supplying the hemolytic agent from either one of the reagent tank 33a (33c, 33e, 33g, 33i) or the reagent tank 33b (33d, 33f, 33h, 33j). Then, the switching valve 25a is provided with an electromagnetic valve 251a for opening and closing the flow passage through which the hemolytic agent sent out from the reagent tank 33a flows, and an electromagnetic valve 252a for opening and closing the flow passage through which the hemolytic agent sent out from the reagent tank 33b flows. Also, the switching valves 25b to 25e are provided with two same electromagnetic valves as the electromagnetic valve 251a and the electromagnetic valve 252a, respectively. Thus, by the switching valves 25a to 25e, after the hemolytic agent is supplied to the hematocyte counting apparatuses 3 until the hemolytic agent in one of the reagent tanks becomes empty, the hemolytic agent in the other tank can be continuously supplied to the hematocyte counting apparatuses 3. Note that whether or not the hemolytic agent in each of the reagent tanks 33a to 33j is empty is detected by float switches 34a to 34j disposed in each of the reagent tanks 33a to 33j.

Figure 5:
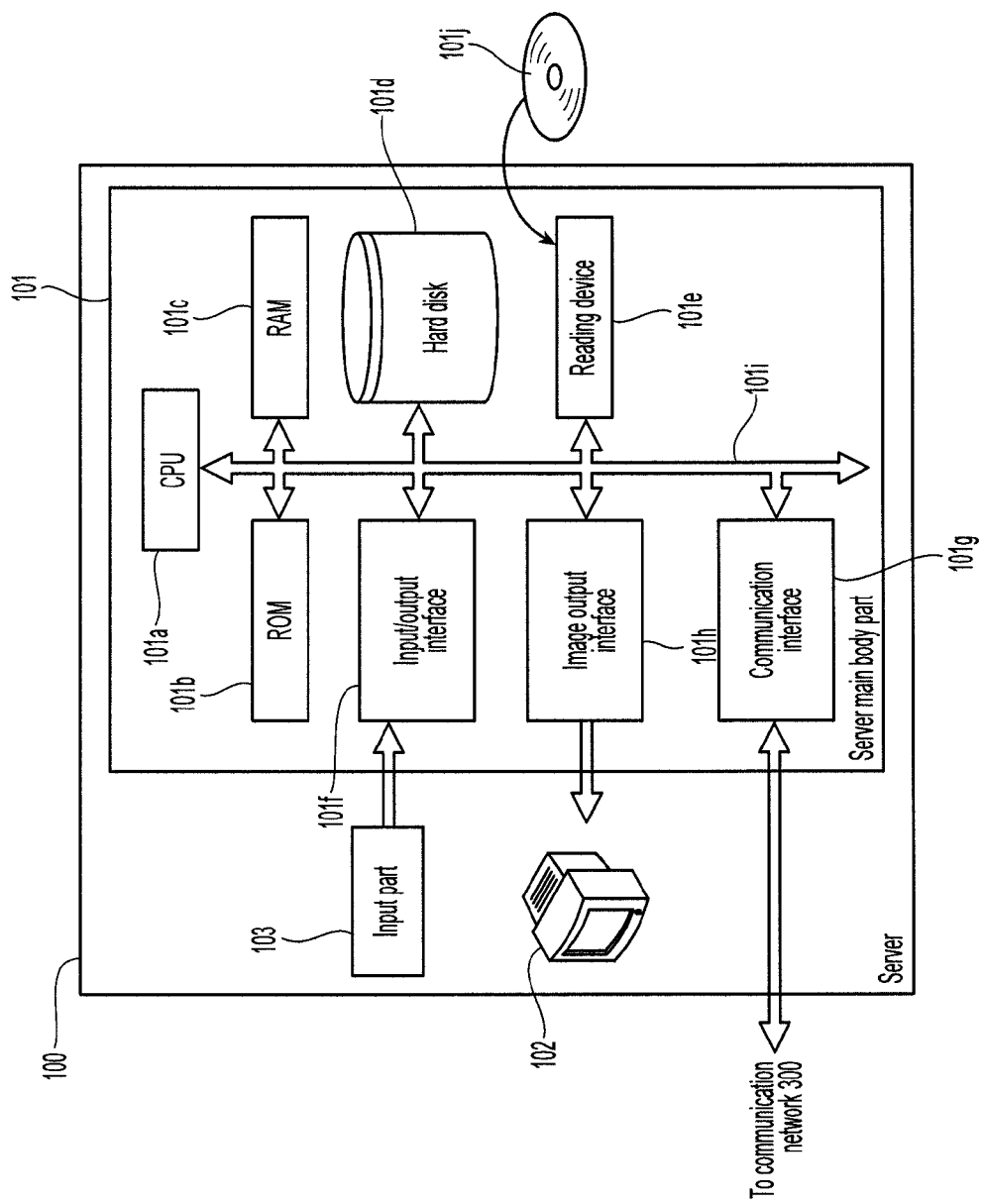
FIG. 5 is a block diagram of a server of the analyzing system according to one embodiment as shown in FIG. 1.
Figure 6:
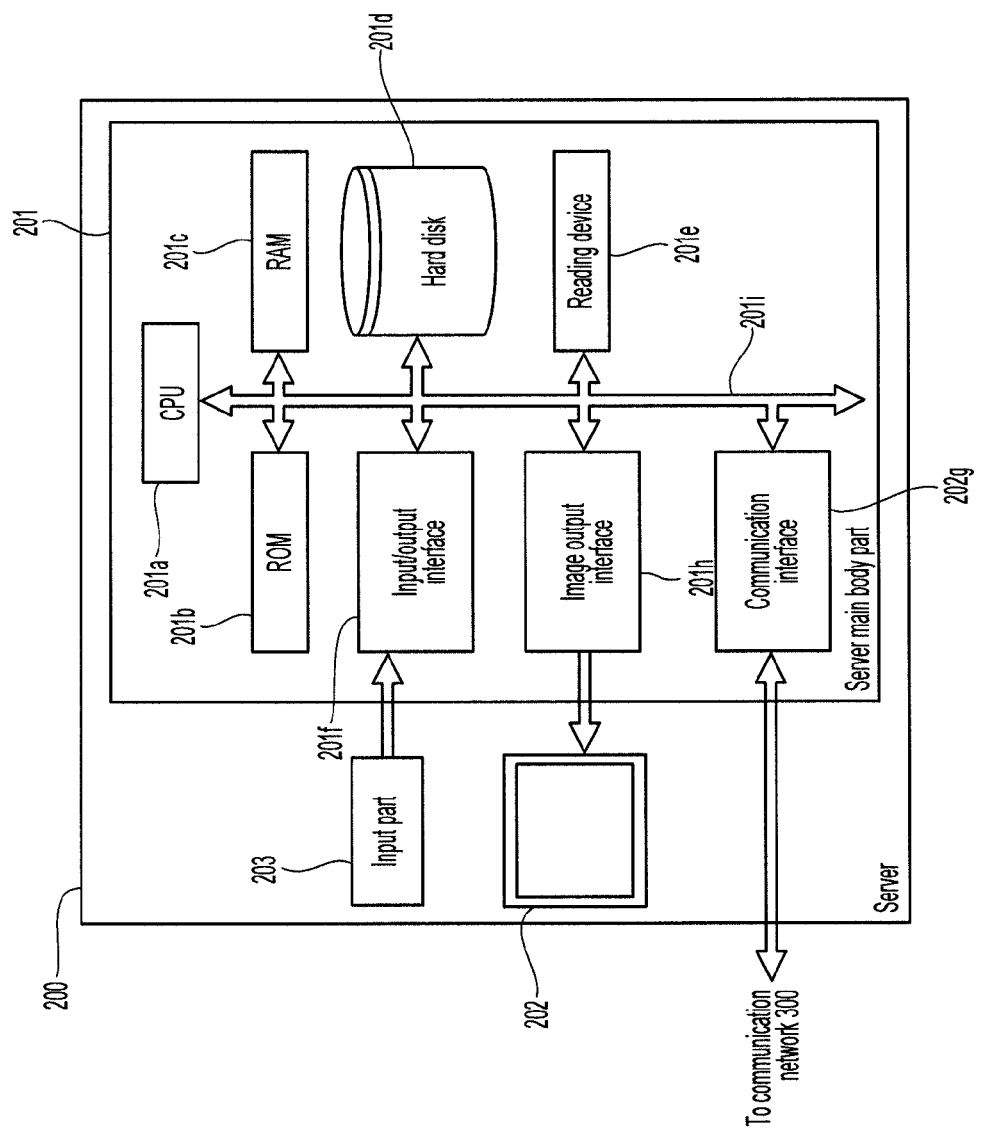
FIG. 6 is a block diagram of a client computer of the analyzing system according to one embodiment as shown in FIG. 1.

Next, the constitution of the server 100 will be explained. The server 100 (see FIG. 1 and FIG. 2) is a Web server, and is provided for storing information transmitted from the reagent preparation apparatus 10 and the reagent feeding apparatus 30 of each inspection line 1 to 9, and transmitting the stored information through a communication network 300 responding to a request of the client computer 200. As shown in FIG. 5, the server 100 is mainly composed of a server main body part 101, a display part 102, and an input part 103. The server main body part 101 is mainly composed of a CPU 101a, a ROM 101b, a RAM 101c, a hard disk 101d, a reading device 101e, an input/output interface 101f, a communication interface 101g, and an image output interface 101h, wherein the CPU 101a, the ROM 101b, the RAM 101c, the hard disk 101d, the reading device 101e, the input/output interface 101f, the communication interface 101g, and the image output interface 101h are connected by a bus 101i.

The CPU 101a is capable of executing a computer program stored in the ROM 101b and a computer program loaded into the RAM 101c. Then, by executing a Web server program by this CPU 101a, the server 100 functions as the Web server.

The ROM 101b is composed of a mask ROM, PROM, EPROM, and EEPROM, etc., and stores the computer program executed by the CPU 101a and data used therefore.

The RAM 101c is composed of a SRAM or a DRAM, etc. A RAM 101c is used for reading the computer program recorded in the ROM 101b and the hard disk 101d. When these computer programs are executed, the RAM 101c is used as a working area of the CPU 101a.

The hard disk 101d has installed therein various kinds of computer programs to be executed by the CPU 101a, such as the operating system, application programs, etc., and data used for executing these computer programs.

A reading device 101e is constituted of a flexible disk drive, a CD-ROM drive, or a DVD-ROM drive, etc., and is capable of reading the computer program or data recorded on a portable recording medium 101j. In addition, the portable recording medium 101j has stored therein an application program whereby the server 100 functions as a server device, and the server 100 can read the application program according to this embodiment from this portable recording medium 101j and install this application program on the hard disk 101d.

Note that the application program is not only supplied by the portable recording medium 101j, but also can be supplied through the electric communication circuit (whether it is by a cable or radio) from an external apparatus connected to the client computer 200 so as to be communicated with each other by the aforementioned electric communication circuit. For example, when the application program is stored in the hard disk of the server computer on the internet, it is possible to access this server computer by the server 100 of this embodiment, download the corresponding application program, and install it on the hard disk 101d.

On the hard disk 101d, for example, an operating system of providing a graphical user interface environment by a window system such as a Windows (registered trademark) produced and distributed by US Microsoft, or an Unix (registered trademark) operating system and an X window system, being a window system operating on this operating system, are installed.

The input/output interface 101f is constituted of, for example, a serial interface such as an USB, an IEEE1394, an RS-232C, a parallel interface such as a SCSI, an IDE, and an IEEE1284, and an analogue interface composed of a D/A converter and an A/D converter, etc. The input part 103 composed of a keyboard and a mouse is connected to the input/output interface 101f, and by using this input part 103 by a user such as an operator, a manager, a user supervisor, and a maintenance technician, etc., the data can be inputted in the server 100.

The communication interface 101g is an Ethernet (registered trademark) interface, for example. By this communication interface 101g, data transmission/reception by the server 100 is possible between the server and apparatuses (the reagent preparation apparatus 10, the reagent feeding apparatus 30, and the client computer 200) connected to the communication network 300 by using a predetermined communication protocol.

The image output interface 101h is connected to the display part 102 constituted of an LCD or a CRT, etc., and outputs an image signal to the display part 102 in accordance with image data supplied from the CPU 101a. The display part 102 displays an image (screen) by following the image signal thus inputted.

Next, the constitution of the client computer 200 will be explained. The client computer 200 is connected to the server 100 (see FIG. 1), being a Web server, through the communication network 300 (see FIG. 1), and serves as a personal computer on which a Web browser for browsing the information stored in the server 100 is installed. As shown in FIG. 1, this client computer 200 is mainly constituted of a main body part 201, a display part 202, and an input part 203. The main body part 201 is mainly constituted of a CPU 201a, an ROM 201b, an RAM 201c a hard disk 201d, a reading device 201e, an input/output interface 201f, a communication interface 201g, and an image output interface 201h, wherein the CPU 201a, the ROM 201b, the RAM 201c, the hard disk 201d, the reading device 201e, the input/output interface 201f, the communication interface 201g, and the image output interface 201h are connected by a bus 201i.

The CPU 201a can execute the computer program stored in the ROM 201b and the computer program loaded on the RAM 201c. Then, by executing the application program of the Web browser by this CPU 201a, the client computer 200 functions as a client.

The ROM 201b is constituted of a mask ROM, a PROM, an EPROM, and an EEPROM, etc., and the computer program executed by the CPU 201a and the data used therefore are stored therein.

The RAM 201c is constituted of a SRAM or a DRAM, etc. The RAM 201c is used for reading the computer program recorded in the ROM 201b and the hard disk 201d, and is used as the working area of the CPU 201a when these computer programs are executed.

The hard disk 201d has installed therein various computer programs to be executed by the CPU 201a, such as the operating system and an application program of the Web browser, and the data used for executing these computer programs.

In addition, on the hard disk 201d, for example, the operating system of providing the graphical user interface environment by the window system such as a Windows (registered trademark) produced and distributed by US Microsoft, or the Unix (registered trademark) operating system and the X window system, being a window system that operates on this operating system, are installed. In the explanation given hereunder, the application program of the Web browser is assumed to be operated on such a window system.

The reading device 201e is constituted of a flexible disk drive, a CD-ROM drive, or a DVD-ROM drive, etc.

The input/output interface 201f is, for example, constituted of the serial interface such as USB, IEEE1394, RS-232C, the parallel interface such as SCSI, IDE, and IEEE1284, and the analogue interface composed of the D/A converter and the A/D converter, etc. The input part 203 composed of the keyboard and mouse is connected to the input/output interface 201f, and by using this input part 203 by the operator, manager, user supervisor, and maintenance technician, etc., the data can be inputted in the client computer 200.

The communication interface 201g is, for example, the Ethernet (registered trademark) interface. By this communication interface 201g, the client computer 200 is connected to the communication network 300 by using a predetermined communication protocol, to make it possible to transmit/receive data between the client computer and the apparatuses (the reagent preparation apparatus 10, the reagent feeding apparatus 30, and the server 100).

The image output interface 201h is connected to the display part 202 constituted of the LCD or the CRT, etc., and outputs to the display part 202 the image signal corresponding to the image data supplied from the CPU 201a. The display part 202 displays the image (screen) by following the image signal thus inputted.

The CPU 201a requests a transmission of the information stored in the server 100 by using the installed Web browser, and thus receives the information transmitted from the server 100 that receives a transmission request, and displays the information thus received on the display part 202.

FIG. 7 to FIG. 12 are views showing the screen displayed on the display part of the client computer of the analyzing system according to one embodiment shown in FIG. 1. Next, with reference to FIG. 7 to FIG. 12, an explanation will be given to details of the screens (an apparatus state screen 400a (initial screen), a preparation apparatus state detailed screen 400b, a reagent feeding apparatus state detailed screen 400c, a preparation history screen 400d, a preparation error history screen 400e, and a reagent feeding error history screen 400f) that are displayed on the display part 202 of the client computer 200.

The apparatus state screen 400a (see FIG. 7) is the initial screen when activating the client computer 200 connected to the server 100 so as to be communicated with each other. In this apparatus state screen 400a, it is possible to confirm an operation state of nine reagent preparation apparatuses 10 provided on each of the inspection lines 1 to 9, the remaining amount of the concentrated reagent used in the reagent preparation apparatuses 10, an operation state of eight reagent feeding apparatuses 30 provided on each of the inspection lines 1 to 8, and existence/non-existence of the hemolytic agent sent out by the reagent feeding apparatuses 30.

Figure 7:
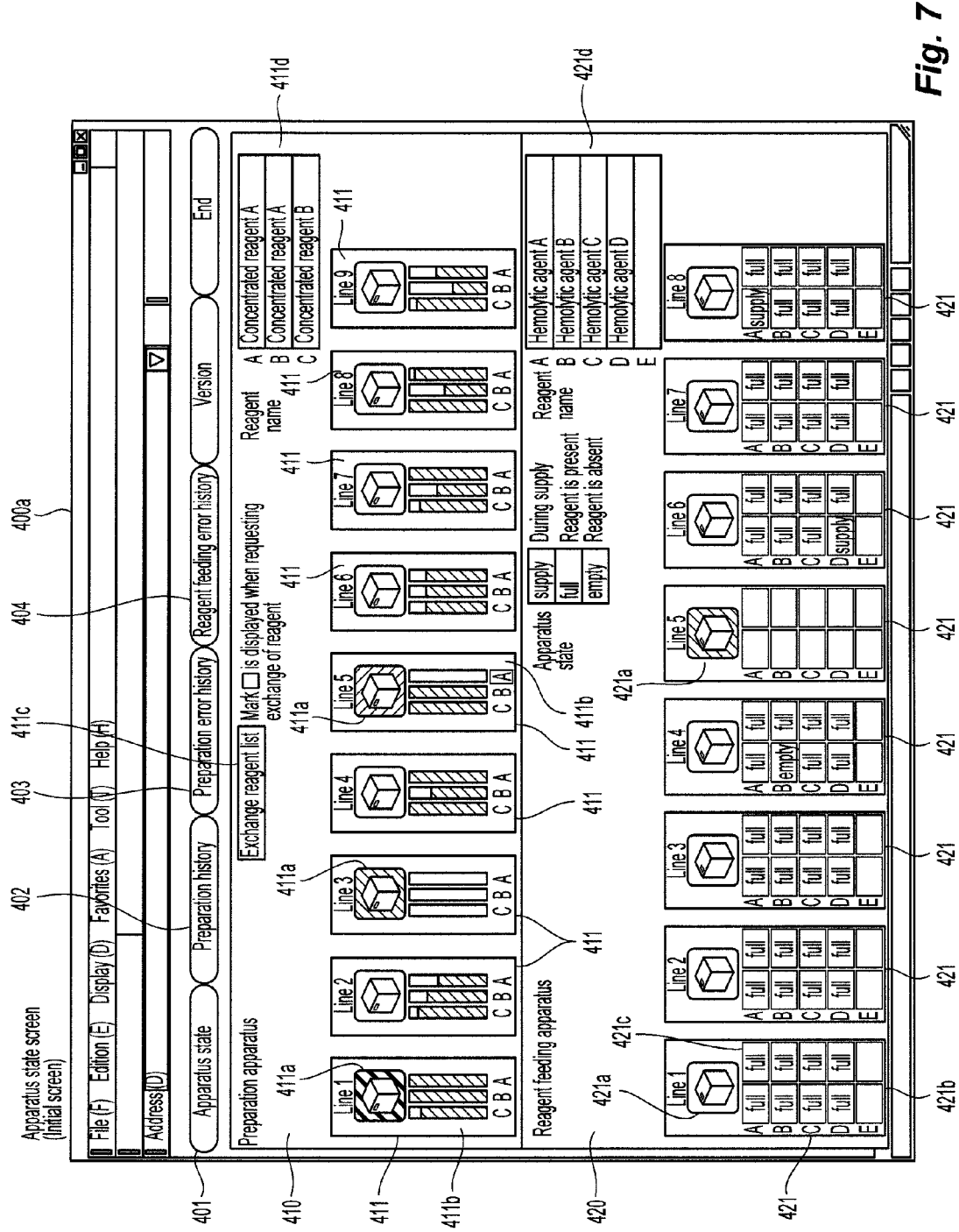
FIG. 7 is a view showing a screen (apparatus state screen) displayed on a display part of the client computer of the analyzing system according to one embodiment as shown in FIG. 1.
Figure 8:
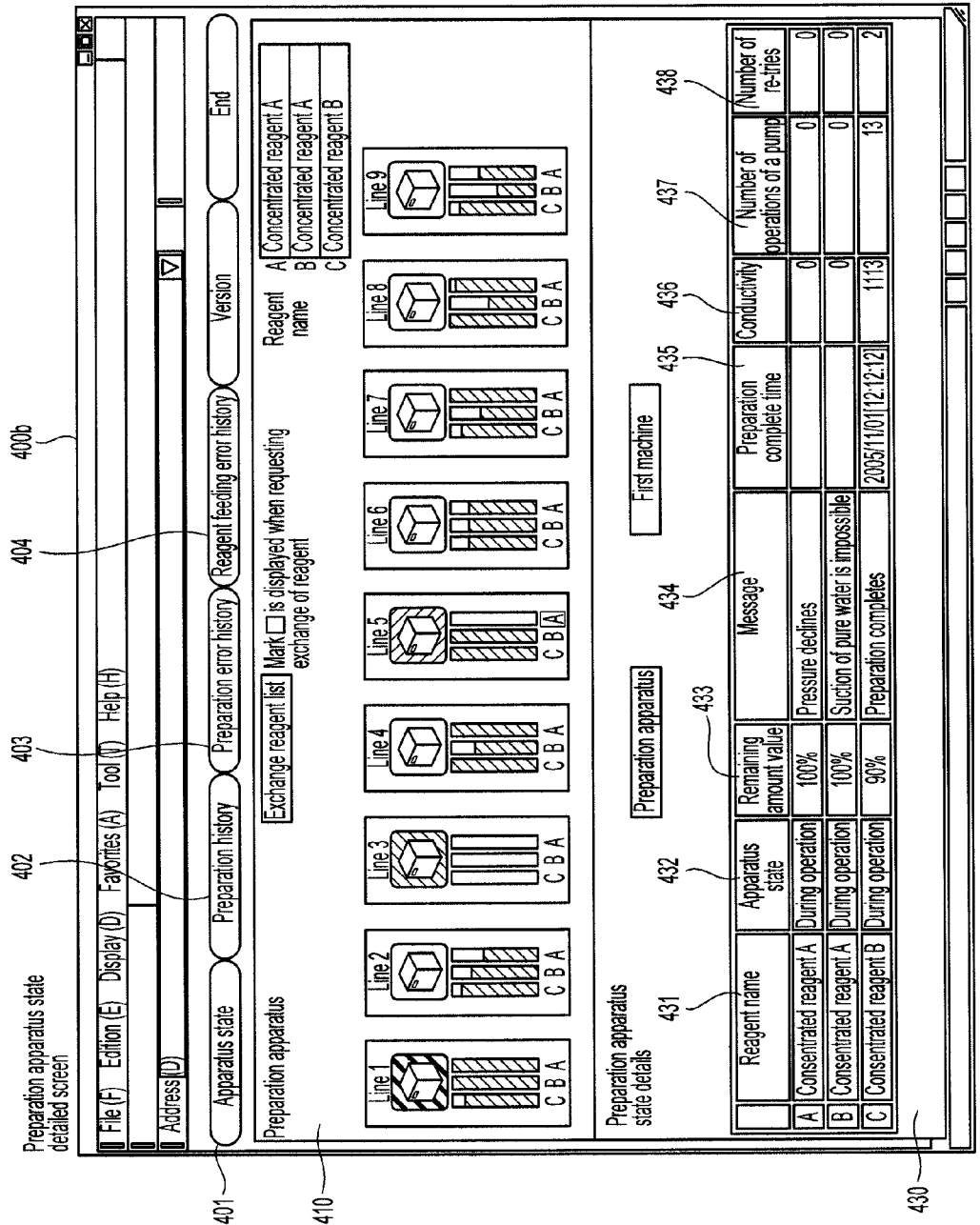
FIG. 8 is a view showing a screen (preparation apparatus state detailed screen) displayed on the display part of the client computer of the analyzing system according to one embodiment as shown in FIG. 1.
Figure 9:
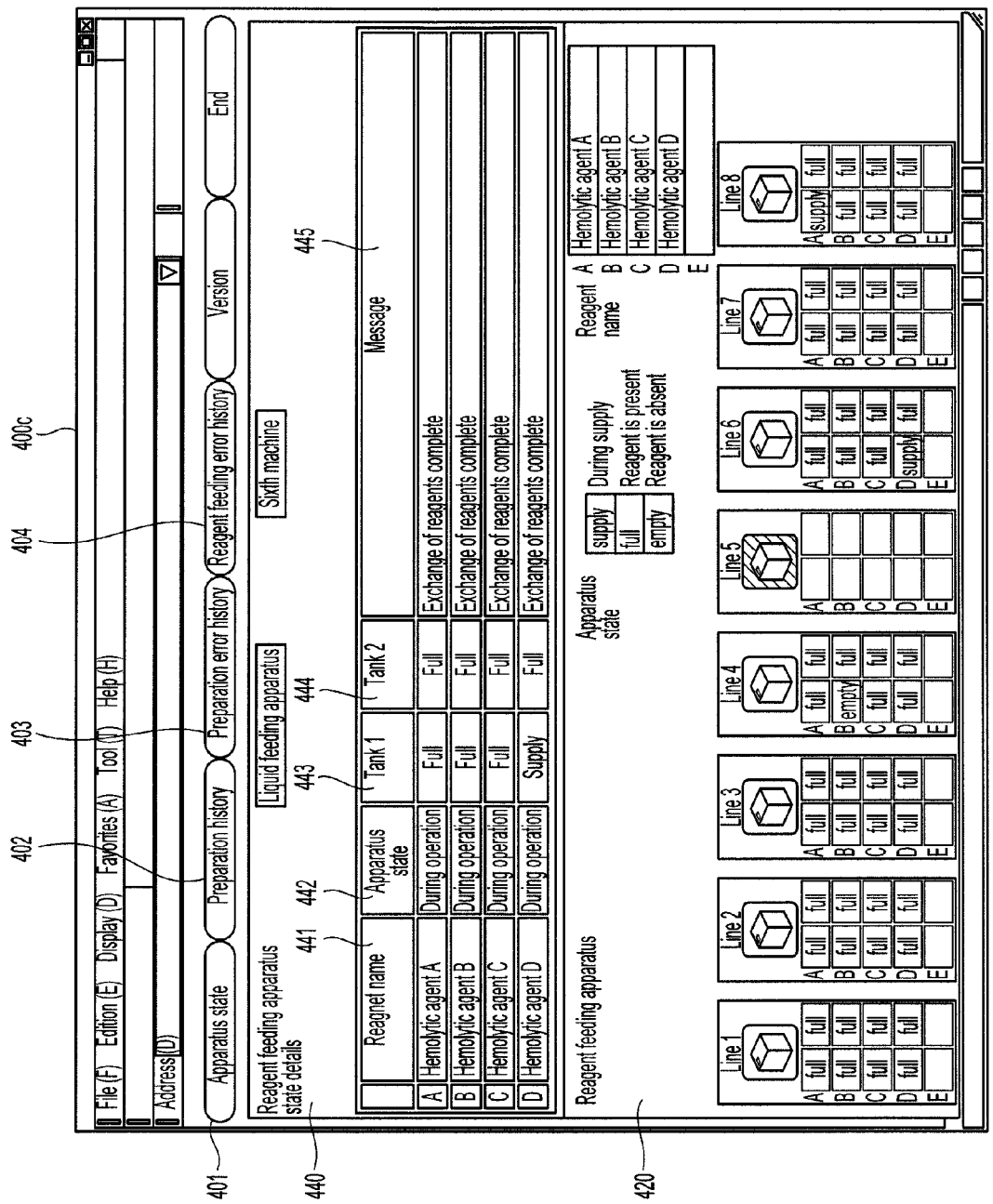
FIG. 9 is a view showing a screen (reagent feeding apparatus state detailed screen) displayed on the display part of the client computer of the analyzing system according to one embodiment as show in FIG. 1.
Figure 12:
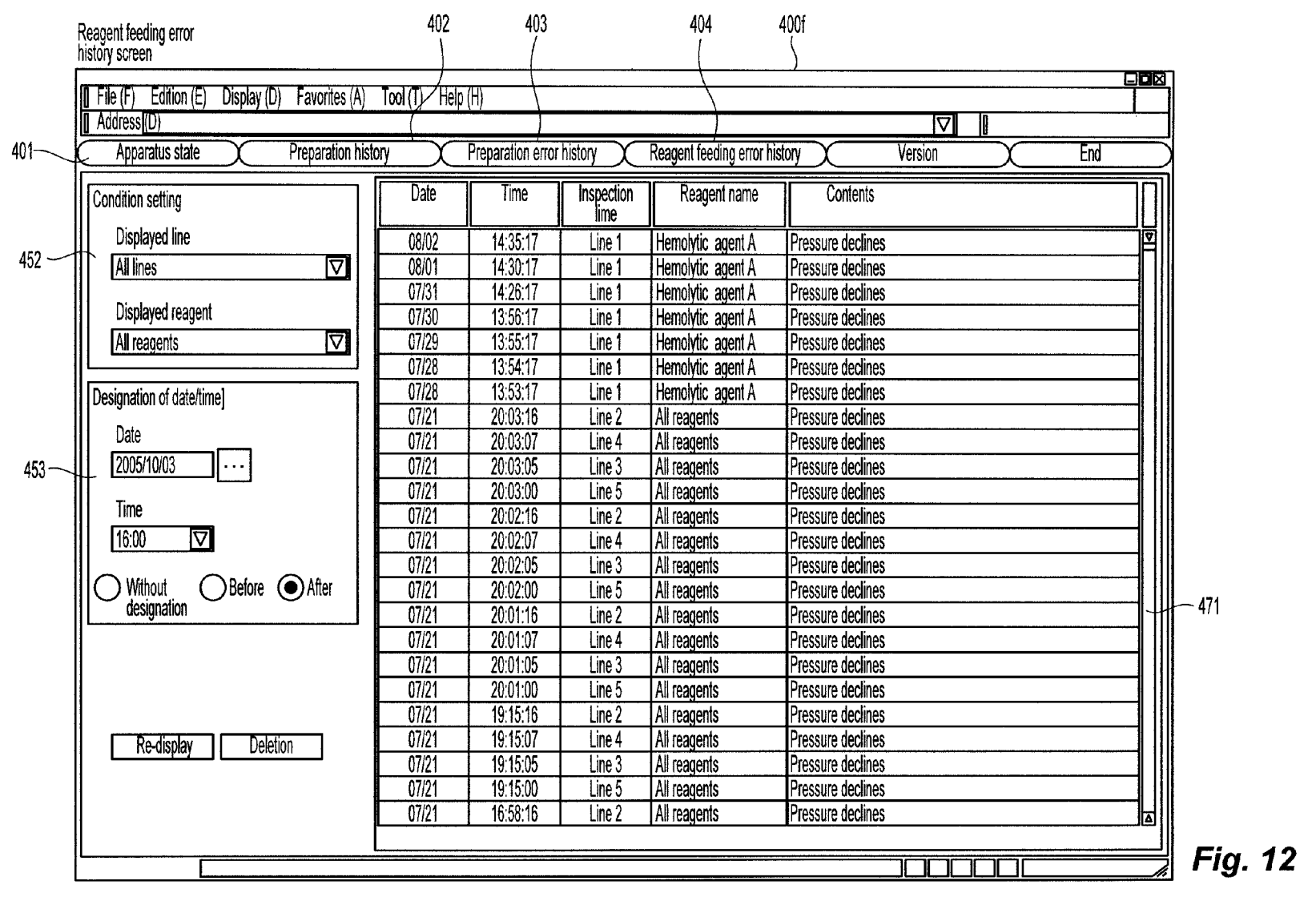

As shown in FIG. 7, an apparatus state button 401 for displaying the screen (apparatus state screen 400a), a preparation history button 402 for displaying the preparation history screen 400d (see FIG. 10), a preparation error history button 403 for displaying the preparation error history screen 400e (see FIG. 11), and a reagent feeding error history button 404 for displaying the reagent feeding error history screen 400f (see FIG. 12) are displayed on the apparatus state screen 400a.

Then, the apparatus state screen 400a as shown in FIG. 7 is provided with a preparation apparatus information display part 410 for displaying each kind of information regarding the reagent preparation apparatus 10, and a reagent feeding apparatus information display part 420 on which each kind of information regarding the reagent feeding apparatus 30 is displayed.

The preparation apparatus information display part 410 is provided with an inspection line information display part 411 on which the operation state of the reagent preparation apparatus 10 provided in the inspection line 1 (see FIG. 2) in the inspection center, and the remaining amount of the concentrated reagent used in the reagent preparation apparatus 10 are displayed. Then, the inspection line information display part 411 displays an icon 411a showing an outer appearance of the reagent preparation apparatus 10, and a remaining amount display part 411b showing by a graph the remaining amount of the concentrated reagent stored in each of the three storing parts 31a to 31c (see FIG. 3). In addition, the icon 411a shows the operation state of the reagent preparation apparatus 10 by changing a background color of the outer appearance of the apparatus. Specifically, yellow color is displayed when the reagent preparation apparatus 10 is initialized, green color is displayed when the reagent preparation apparatus 10 is set in stand-by mode, blue color is displayed when the reagent preparation apparatus 10 is in the middle of operating, red color is displayed when abnormality occurs, and gray color is displayed when the communication is interrupted, as the color of the outer appearance of the apparatus of the icon 411a. Also, in the preparation apparatus information display part 410, the same inspection line information display part 411 as the inspection line information display part 411 for the aforementioned inspection line 1 is provided for each reagent preparation apparatus 10 provided on the inspection lines 2 to 9.

Note that in FIG. 7, the icon 411a of the inspection line information display part 411 of the inspection line 1 is displayed in red color (area shown by thick hatched lines), and the operator can confirm abnormality occurring in the reagent preparation apparatus 10 of the inspection line 1. Also, the icon 411a of the inspection line information display part 411 of the inspection line 3 is displayed in gray color (area shown by thin hatching lines in an obliquely upper right direction), and the operator can confirm that the communication between the reagent preparation apparatus 10 of the inspection line 3 and the server 100 (see FIG. 1) is interrupted. Also, the icon 411a of the inspection line information display part 411 of the inspection line 5 is displayed in green color (area shown by thin hatched lines in an obliquely upper left direction), and the operator can confirm that the reagent preparation apparatus 10 of the inspection line 5 is set in a stand-by mode. Then, the icon 411a of the inspection line information display part 411 of the inspection line 2, inspection line 4, and the inspection lines 6 to 9 is displayed in blue color (area without hatching lines), and the operator can confirm that each reagent preparation apparatus 10 of the inspection line 2, inspection line 4, and the inspection lines 6 to 9 is normally operated.

Three graphs of the remaining amount display part 411b are displayed so as to correspond to the three storing parts 31a to 31c (see FIG. 3) in which the concentrated reagent is stored. Specifically, the graph corresponding to the number "A" assigned to the remaining amount display part 411b shows the remaining amount of the concentrated reagent A stored in the storing part 31a, and the graph corresponding to the number "B" shows the remaining amount of the concentrated reagent A stored in the storing part 31b, and the graph corresponding to the number "C" shows the remaining amount of a concentrated reagent B stored in the storing part 31c. Also, a mark "□" to request an exchange of the reagent is assigned to the number "A" of the remaining amount display part 411b of the inspection line information display part 411 of the inspection line 5. Thus, it is possible for the operator to confirm the mark "□" assigned to the number "A" of the remaining amount display part 411b and to confirm a necessity of exchanging the concentrated reagent.

In addition, the preparation apparatus information display part 410 is provided with an exchange reagent list button 411c for displaying as a list the remaining amount of the concentrated reagent used in the reagent preparation apparatus 10, a presence/absence of the hemolytic agent used in the reagent feeding apparatus 30 and the number of emptied reagents (concentrated reagent and hemolytic agent), and an concentrated reagent name display column 411*d* for displaying a name of the concentrated reagent stored in each of the three storing parts 31*a* to 31*c* (see FIG. 3). Accordingly, the operator can confirm that the concentrated reagent stored in the storing part 31*a* and the storing part 31*b* used in each reagent preparation apparatus 10 of the inspection lines 1 to 9 is the "concentrated reagent A", and the concentrated reagent stored in the storing part 31*c* is the "concentrated reagent B".

The reagent feeding apparatus information display part 420 is provided with an inspection line information display part 421 on which the operation state of the reagent feeding apparatus 30 provided on the inspection line 1 (see FIG. 2) in the inspection center and the presence/absence of the hemolytic agent sent out from the reagent feeding apparatus 30 are displayed. Then, the inspection line information display part 421 displays an icon 421*a* showing the outer appearance of the reagent feeding apparatus 30 and a remaining amount display part 421*b* showing by characters the presence/absence of the hemolytic agent stored in each of the ten reagent tanks 33*a* to 33*j* (see FIG. 4). Also, the icon 421*a* shows the operation state of the reagent feeding apparatus 30 by changing the background color of the outer appearance of the apparatus. Specifically, in the same way as the icon 411*a* of the reagent preparation apparatus 10 as described above, yellow color is displayed when the reagent feeding apparatus 30 is initialized, green color is displayed when it is set in a stand-by mode, blue color is displayed when it is in the middle of operating, red color is displayed when abnormality occurs, and gray color is displayed when the communication is interrupted, as the color of the outer appearance of the apparatus of the icon 421*a*. Also, for each reagent feeding apparatus 30 provided on the inspection lines 2 to 8, the reagent feeding apparatus information display part 420 is provided with the same inspection line information display part 421 as the inspection line information display part 421 for the aforementioned inspection line 1.

Note that in FIG. 7, the icon 421*a* of the inspection line information display part 421 of the inspection line 5 is displayed in gray color (area shown by thin hatching lines in an obliquely upper right direction), and the operator can confirm that the communication between the reagent feeding apparatus 30 (see FIG. 1) of the inspection line 5 and the server 100 (see FIG. 1) is interrupted. Then, the icon 421*a* of the inspection line information display part 421 of the inspection lines 1 to 4 and the inspection lines 6 to 8 is displayed in blue color (area without hatching lines), and the operator can confirm that each reagent feeding apparatus 30 of the inspection lines 1 to 4 and the inspection lines 6 to 8 is normally operated.

The remaining amount display part 421*b* is provided with ten remaining amount presence/absence display columns 421*c* for each of the reagent tanks 33*a* to 33*j* (see FIG. 4). Then, in the remaining amount presence/absence display columns 421*c*, "supply" is displayed when the hemolytic agent of the reagent tanks 33*a* to 33*j* is in the middle of supplying by the reagent feeding apparatus 30, "full" is displayed when the hemolytic agent is present, and "empty" is displayed when the hemolytic agent is absent. Note that the "full" and "empty" displayed on the remaining amount presence/absence display column 421*c* are displayed based on the presence/absence of the hemolytic agent detected by the float switches 34*a* to 34*j*. Thus, the operator can confirm the "empty" of the remaining amount presence/absence display column 421*c*, and can confirm the necessity of exchanging the hemolytic agent.

Further, the reagent feeding apparatus information display part 420 is provided with a hemolytic agent name display column 421*d* for displaying the name of the hemolytic agent stored in the reagent tanks 33*a* to 33*j*, and the operator can confirm that the hemolytic agent stored in the reagent tanks 33*a* and 33*b* is a "hemolytic agent A", the hemolytic agent stored in the reagent tanks 33*c* and 33*d* is a "hemolytic agent B", the hemolytic agent stored in the reagent tanks 33*e* and 33*f* is a "hemolytic agent C", and the hemolytic agent stored in the reagent tanks 33*g* and 33*h* is a "hemolytic agent D". Note that in the hematocyte counting apparatuses 3 of this embodiment, other kind of the hemolytic agent excluding the aforementioned hemolytic agent is not used, and therefore the hemolytic agent is not stored in the reagent tanks 33*i* and 33*j* (see FIG. 4).

The preparation apparatus state detailed screen 400*b* (see FIG. 8) is the screen displayed by selecting (clicking by using a mouse not shown) the icon 411*a* (see FIG. 7) of the aforementioned preparation apparatus information display part 410, and the reagent feeding apparatus information display part 420 (see FIG. 7) of the apparatus state screen 400*a* shown in FIG. 7 is switched to the preparation apparatus state detailed part 430. This preparation apparatus state detailed part 430 has a function of displaying a detailed state of the reagent preparation apparatus 10. Note that this embodiment shows a case that the icon 411*a* (see FIG. 7) corresponding to the reagent preparation apparatus 10 of the inspection line 1 is clicked to display the detailed information of the reagent preparation apparatus 10 of the inspection line 1.

The preparation apparatus state detailed part 430 displays a table provided with a field of a reagent name, an apparatus state, a remaining amount value, a message, a preparation complete time, a conductivity, the number of operations of a pump and the number of re-tries for each of three storing parts 31*a* to 31*c* (see FIG. 3). A reagent name column 431 displays the name of the concentrated reagent in the same way as the concentrated reagent name display column 411*d* (see FIG. 7), and an apparatus state column 432 displays a state of the apparatus. Also, a remaining amount value column 433 displays by percentage the remaining amount of the concentrated reagent calculated based on weight data detected by the weight sensors 32*a* to 32*c* (see FIG. 3) having the storing parts 31*a* to 31*c* placed thereon. In addition, a message column 434 displays an error message, etc., generated in the reagent preparation apparatus 10. Note that in this embodiment, the error message showing "a pressure declines" is displayed in the storing part 31*a*, and the error message showing "suction of pure water is impossible" is displayed in the storing part 31*b*. Thus, by confirming the error message showing "a pressure declines", the operator can confirm that the pressure added from a compressor (not shown) for sucking the concentrated reagent A declines in the storing part 31*a* in which the concentrated reagent A is stored. Also, by confirming the error message of "suction of pure water is impossible", the operator can confirm that the pure water blended with the concentrated reagent A supplied from the storing part 31*b* is not sucked. In addition, a preparation complete time column 435 displays the time when the diluted solution prepared by blending pure water and the concentrated reagent shows a desired concentration, and a conductivity column 436 displays the electric conductivity of the diluted solution thus prepared.

Further, a number of operations of a pump column 437 displays the number of operations of the pure water quantity measuring pump 13. Also, a number of re-tries column 438 displays the number of re-preparations so that the electric conductivity of the diluted solution is within a desired range when the electric conductivity of the prepared diluted solution is not within the desired range.

The reagent feeding apparatus state detailed screen 400c (see FIG. 9) is the screen displayed by selecting (clicking by using the mouse not shown) the icon 421a (see FIG. 7) of the aforementioned reagent feeding apparatus information display part 420, and the preparation apparatus information display part 410 of the apparatus state screen 400a shown in FIG. 7 is switched to a reagent feeding apparatus state detailed part 440. This reagent feeding apparatus state detailed part 440 has a function of displaying a detailed state of the reagent feeding apparatus 30 (see FIG. 1). Note that this embodiment shows a case that the icon 421a (see FIG. 7) corresponding to the reagent feeding apparatus 30 of the inspection line 6 is clicked to display the detailed information of the reagent feeding apparatus 30 of the inspection line 6.

The reagent feeding apparatus state detailed part 440 displays a table provided with a field of a reagent name, an apparatus state, a tank 1, a tank 2, and a message, corresponding to the hemolytic agent (four kinds in this embodiment). A reagent name column 441 displays the name of the hemolytic agent in the same way as the hemolytic agent name display column 421d (see FIG. 7), and an apparatus state column 442 displays the state of the apparatus. Also, a tank 1 column 443 and a tank 2 column 444 display any one of the "supply", "empty", or "full" in the same way as the remaining amount presence/absence display column 421c (see FIG. 7). In addition, a message column 445 displays the error message generated in the reagent feeding apparatus 30. Note that in this embodiment, the message showing "exchange of reagent completes" is shown for all the hemolytic agents.

The preparation history screen 400d (see FIG. 10) is the screen displayed by selecting the preparation history button 402 displayed on each screen shown in FIG. 7 to FIG. 12. This preparation history screen 400d is the screen for displaying a preparation history of a normally prepared concentrated reagent in the reagent preparation apparatus 10 (see FIG. 1) provided on each of the inspection lines 1 to 9. This preparation history screen 400d is provided with a preparation history list part 451 of a table format provided with a field of date, time, inspection line, reagent name, message, conductivity, and the number of operations of a pump and the number of re-tries; a condition setting part 452 for selecting the preparation history of the concentrated reagent displayed in the preparation history list part 451 from the inspection line and the reagent name; and a date/time designation part 453 for selecting the preparation history of the concentrated reagent displayed in the preparation history list part 451 from the date and time of preparation.

The condition setting part 452 is provided with a box 452a capable of selecting "inspection line 1", "inspection line 2" . . . "inspection line 9", and "all lines", etc. For example, by selecting the "inspection line 1" in the box 452a, by using the mouse, etc., by the operator, the preparation history of the concentrated reagent prepared by the reagent preparation apparatus 10 provided on the inspection line 1 is displayed in the preparation history list part 451. In addition, the condition setting part 452 is provided with a box 452b capable of selecting the "concentrated reagent A", "concentrated reagent B", and "all reagents". For example, by selecting the "concentrated reagent A" in the box 452b by the operator by using the mouse, etc., the preparation history of the concentrated reagent A prepared by each reagent preparation apparatus 10 is displayed in the preparation history list part 451. Note that this embodiment shows the state that the "all lines" in the box 452a and the "all reagents" in the box 452b are selected.

The date/time designation part 453 is provided with a calendar display button 453a for displaying a calendar (not shown) for designating the date, and by selecting the date in this calendar, a selected date ("2005/10/03" in the screen) is displayed in a text box 453b. Also, the date/time designation part 453 is provided with a box 453c capable of selecting "0:00", "1:00" . . . "23:00", etc. Further, the date/time designation part 453 is provided with a designation method selecting part 453d capable of selecting any one of "without designation", "before", and "after". For example, by selecting "2005/10/03" by the aforementioned calendar display button 453a and selecting "16:00" in the box 453c of the date/time designation part 453, and selecting "after" of the designation method selecting part 453d, using the mouse, etc., by the operator, the preparation history of the concentrated reagent prepared after "16:00" of "2005/10/03" is displayed in the preparation history list part 451.

Also, the date and time when the concentrated reagent is prepared is displayed in the field of the date and the field of the time of the preparation history list part 451 of the preparation history screen 400d. In addition, the inspection line provided with the reagent preparation apparatus 10 is displayed in the field of the inspection line of the preparation history list part 451. Further, the same content as, a reagent name column 431, a message column 434, a conductivity column 436, a number of operations of a pump column 437, and a number, of re-tries column 438 shown in the preparation apparatus state detailed screen 400b (see FIG. 8) is displayed respectively in each field of the reagent name, message, conductivity, the number of operations of pump, and the number of re-tries of the preparation history list part 451.

The preparation error history screen 400e (see FIG. 11) is the screen displayed by selecting the preparation error history button 403 displayed in each screen shown in FIG. 7 to FIG. 12. This preparation error history screen 400e is the screen for displaying the preparation history of the concentrated reagent where an error occurs during preparation, in the reagent preparation apparatus 10 provided on each inspection line 1 to 9. As shown in FIG. 11, this preparation error history screen 400e is provided with a preparation error history list part 461 of a table format provided with a field of the date, time, inspection line, reagent name, content, and the same condition setting part 452 and the date/time designation part 453 as those shown in the preparation history screen 400 of FIG. 10.

In addition, the same contents as those shown in the field of the date, the field of the time, the field of the inspection line, and the field of the reagent name of the preparation history list part 451 of the aforementioned reparation history screen 400d (see FIG. 10) is displayed in the field of the date, the field of the time, the field of the inspection line, and the field of the reagent name of the preparation history list part 461 of the preparation error history screen 400e. Also, the same content as that of the error message displayed in the message column 434 (see FIG. 8) shown in the preparation apparatus state detailed screen 400b is shown in the field of the content of the preparation error history list part 461.

The reagent feeding error history screen 400f (see FIG. 12) is the screen displayed by selecting the reagent feeding error history button 404 displayed in each screen shown in FIG. 7 to FIG. 12. This reagent feeding error history screen 400f is the screen for displaying a reagent feeding history of the hemolytic agent that allows a reagent feeding error to occur in the reagent feeding apparatus 30 provided on the inspection lines 1 to 8. This reagent feeding error history screen 400f is provided with a reagent feeding error history list part 471 of a table format provided with the field of the date, time, inspection line, reagent name, and content, and the same condition setting part 452 and a date/time designation part 453 as those shown in the aforementioned preparation history screen 400d (see FIG. 10) and the preparation error history screen 400e (see FIG. 11).

Also, the same contents as those shown in the field of the date, the field of the time, the field of the inspection line, and the field, of the reagent name of the aforementioned preparation history screen 400d (see FIG. 10) and the preparation error history screen 400e (see FIG. 11) are displayed in the field of the date, the field of the time, the field of the inspection line, and the field of the reagent name of the reagent feeding error history list part 471 of the reagent feeding error history screen 400f. In addition, the same content as that of the error message displayed in the message column 445 (see FIG. 9) shown in the reagent feeding apparatus state detailed screen 400c is shown in the field of the content.

Figure 13:
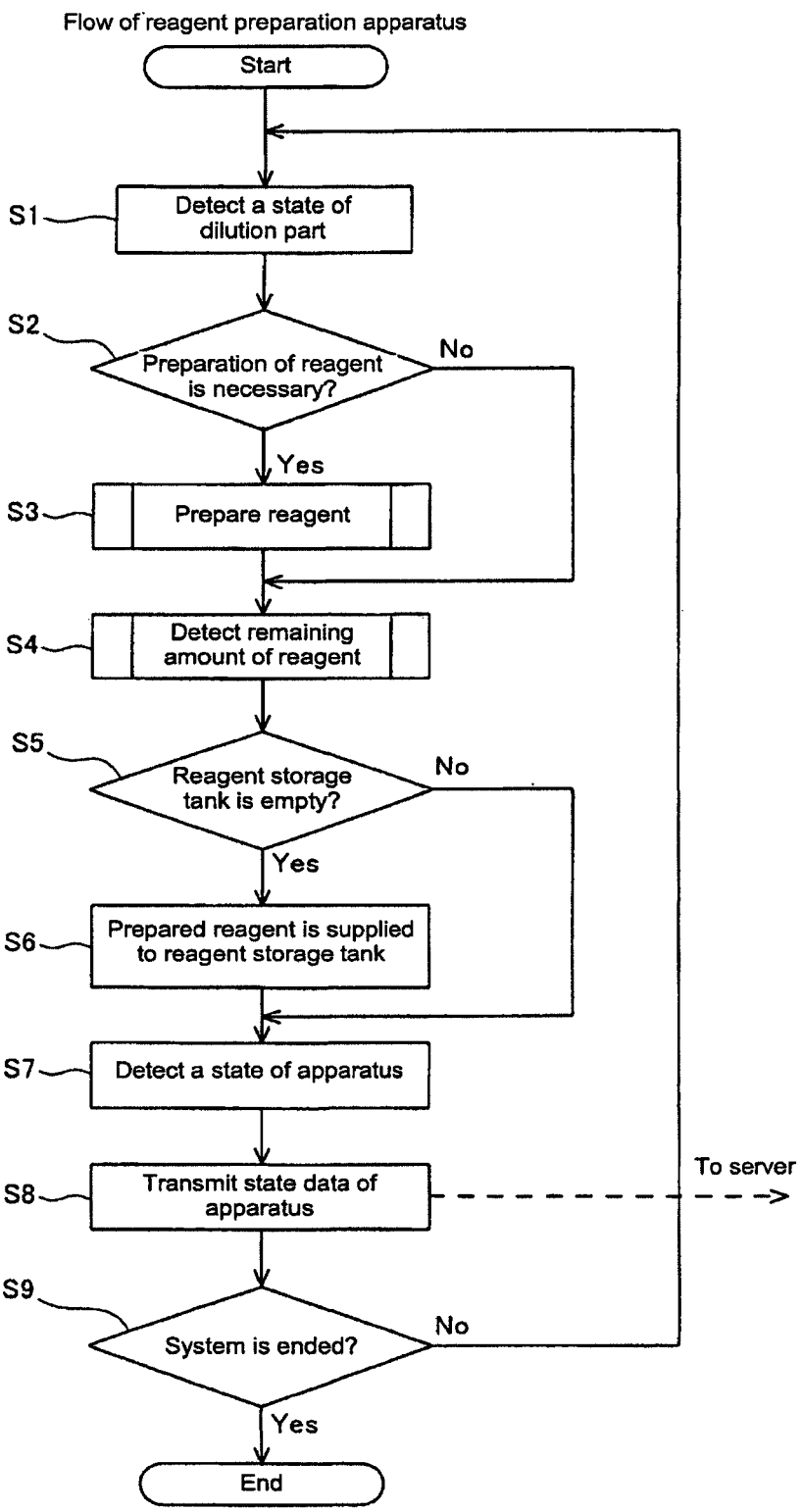
FIG. 13 is a flowchart showing an operation flow of the reagent preparation apparatus of the analyzing system according to one embodiment as shown in FIG. 1.

FIG. 13 is a flowchart showing an operation flow of the reagent preparation apparatus of the analyzing system according to one embodiment shown in FIG. 1. Next, the operation of the reagent preparation apparatus 10 of the analyzing system 1 according to one embodiment of the present invention will be explained with reference to FIG. 1, FIG. 2, FIG. 3, and FIG. 13.

First, in step S1, a state of the dilution part 16, to which the pure water and the concentrated reagent are supplied, is detected by the controller 23. Then, in step S2, whether or not there is a necessity of blending the concentrated reagent and the pure water to prepare the diluted solution is determined. In this step S2, when the request to supply the diluted solution is received from the hematocyte counting apparatuses 3 (see FIG. 1 and FIG. 2) and the blood sample smearing apparatus 4 (see FIG. 2), this is the case that the diluted solution needs to be prepared. Then, in step S2, when it is so determined that there is the necessity for preparing the diluted solution, the diluted solution of a desired electric conductivity is prepared in step S3.

Then, in this embodiment, when it is so determined that the diluted solution needs not to be prepared in step S2, and when the diluted solution of a desired electric conductivity is acquired in step S3, the weight data of the storing parts 31a to 31c is received from the weight sensors 32a to 32c on which the storing parts 31a to 31c storing the concentrated reagent are respectively placed in step S4. Then, based on the weight data thus received, the remaining amount of the concentrated reagent is detected.

In this embodiment, in step S5, whether or not the reagent storage tank 19 shown in FIG. 3 is empty is determined. When the reagent storage tank 19 is determined to be empty in step S5, the diluted solution of a desired electric conductivity is supplied to the reagent storage tank 19 in step S6. Note that when it is so determined that the reagent storage tank 19 is not empty in step S5, this is the case that the diluted solution of a desired electric conductivity has already been stored in the reagent storage tank 19. Thereafter, the diluted solution stored in the reagent storage tank 19 is supplied to each hematocyte counting apparatus 3 or the blood sample smearing apparatus 4. Thereafter, in step S7, the state of the reagent preparation apparatus 10 (in the middle of operating or during shutdown of the apparatus) is detected, and the state of the apparatus thus detected in the step S7 is transmitted to the server 100 as apparatus state data in the step S8. Thereafter, when this state data is transmitted to the client computer 200 (see FIG. 1) from the server 100, background colors of the icon 411a and the icon 421a displayed on the apparatus state screen 400a (see FIG. 7), the preparation apparatus state detailed screen 400b (see FIG. 8), and the reagent feeding apparatus state detailed screen 400c (see FIG. 9) are changed and also the display of the apparatus state column 432 (see FIG. 8) and the display of the apparatus state column 442 (see FIG. 9) are changed.

Then, the operations of the aforementioned step S1 to step S8 are repeated until the operation of the analyzing system 1 is determined to end in step S9. In this way, the operation of the reagent preparation apparatus 10 is controlled.

Figure 14:
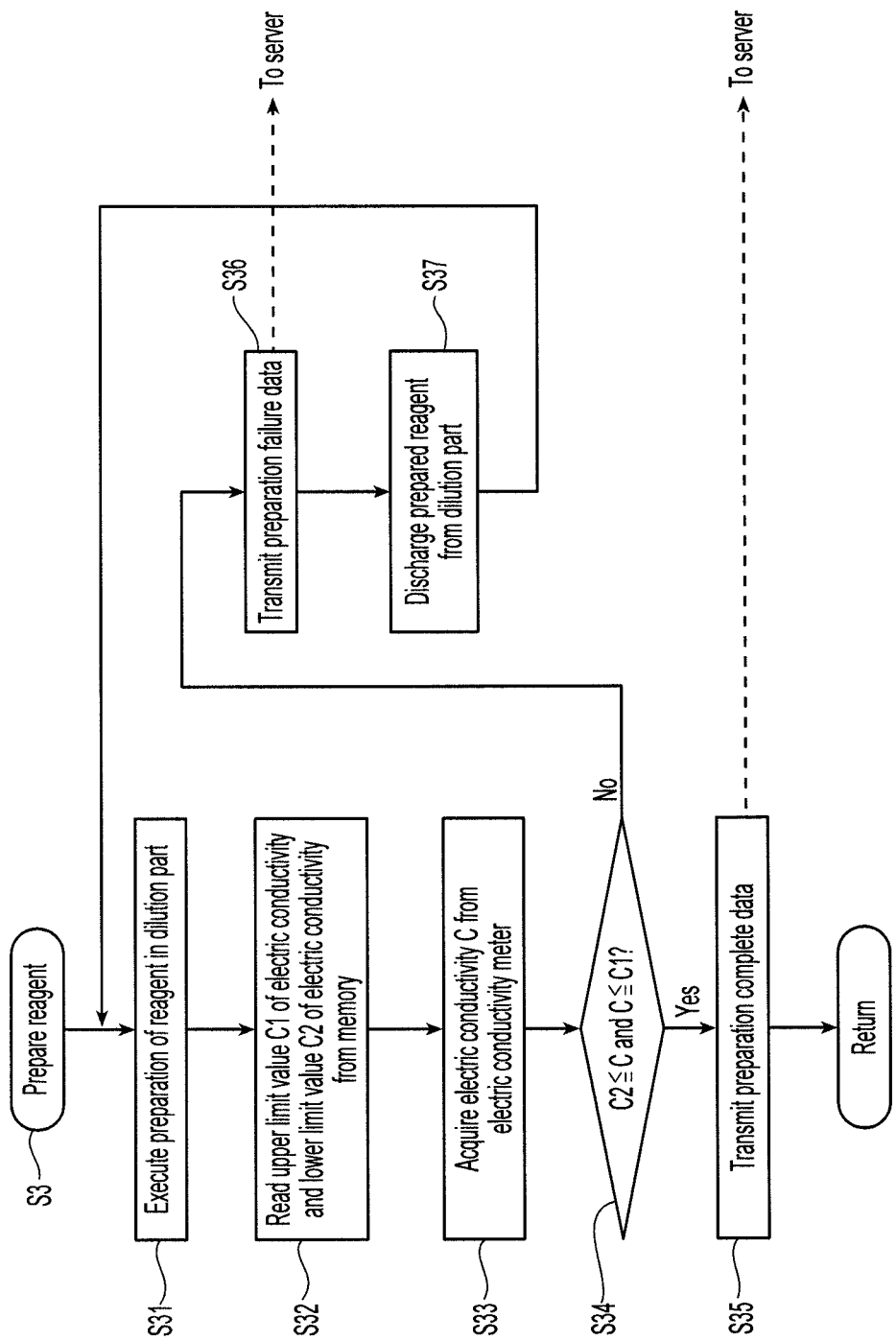
FIG. 14 is a flowchart for explaining details (sub-routine) of preparation of diluted solution as shown in step S3 of FIG. 13.

FIG. 14 is a flowchart for explaining details (sub-routine) of preparation of the diluted solution shown in step S3 of FIG. 13. Next, preparation of the reagent in step S3 of FIG. 13 will be explained in detail, with reference to FIG. 1, FIG. 2, FIG. 3, and FIG. 14.

First, when the diluted solution is prepared, in step S31, the pure water quantitatively measured by the pure water quantity measuring tank 12 (see FIG. 3) is sent to the dilution part 16 (see FIG. 3), and the concentrated reagent quantitatively measured by the reagent quantity measuring tank (see FIG. 3) is sent to the dilution part 16. Then, by stirring the pure water and the concentrated reagent stored in the dilution part 16 by the stirring wing 17a (see FIG. 3) of the stirring part 17, a uniformly blended diluted solution is prepared.

Then, in step S32, the controller 23 (see FIG. 3) reads an upper limit value C1 of the electric conductivity and a lower limit value C2 of the electric conductivity from the memory (not shown) of the controller 23. Note that the upper limit value C1 of the electric conductivity and the lower limit value C2 of the electric conductivity may be stored in the RAM 101c (see FIG. 5) of the server main body part 101 (see FIG. 1 and FIG. 2) of the server 100. Thereafter, in step S33, the controller 23 acquires an electric conductivity C detected by the electric conductivity meter 18 having the detector 18a (see FIG. 3) that comes in contact with the diluted solution in the dilution part 16.

Then, in this embodiment, in step S34, the controller 23 compares the upper limit value C1 of the electric conductivity and the lower limit value C2 of the electric conductivity thus read, and the electric conductivity C of the diluted solution thus acquired. Specifically, the controller 23 determines whether or not the electric conductivity C of the diluted solution is equal to or more than the lower limit value C2 of the read electric conductivity, and also determines whether or not it is equal to or less than the read upper limit value C1 of the electric conductivity. Then, in step S34, when the electric conductivity C of the diluted solution is equal to or less than the upper limit value C1 and also equal to or more than the lower limit value C2, in step S35, the controller 23 transmits to the server 100 preparation complete data indicating completion of the preparation of the diluted solution. Thereafter, by transmitting this preparation complete data from the server 100 to the client computer 200 (see FIG. 1), the message showing "preparation completion" is displayed in a message field of the preparation history list part 451 (see FIG. 10) displayed in the preparation history screen 400d.

Meanwhile, in step S34, when the electric conductivity C of the diluted solution is neither equal to or less than the upper limit value C1, nor equal to or more than the lower limit value C2, in step S36, the controller 23 transmits to the server 100 preparation failure data indicating failure of the preparation of the diluted solution. Thereafter, in step S37, the diluted solution, whose preparation fails, is discharged from the dilution part 16. Thereafter, the processing is returned to step S31, and the aforementioned operation is executed again, so as to acquire the diluted solution of a desired electric conductivity. In this way, the diluted solution of a desired electric conductivity, in which the pure water and the concentrated reagent are blended, is prepared.

Figure 15:
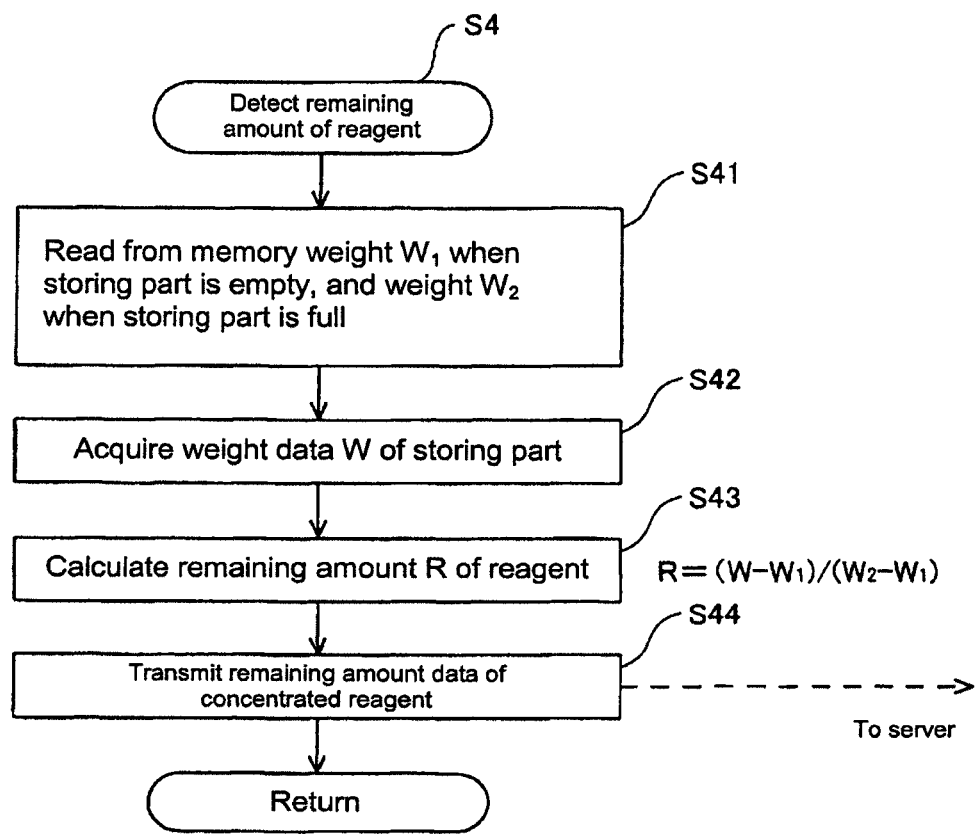
FIG. 15 is a flowchart for explaining details (sub-routine) of a detection method of the remaining amount of the reagent as shown in step S4 of FIG. 13.

FIG. 15 is a flowchart for explaining the details (subroutine) of the detection method of the remaining amount of the reagent shown in step S4 of FIG. 13. Next, detection of the reagent remaining amount in step S4 of FIG. 3 will be explained in detail, with reference to FIG. 1, FIG. 2, FIG. 3, and FIG. 15.

First, in step S41, the controller 23 (see FIG. 3) reads a weight W1 when the storing parts 31a to 31c (see FIG. 3) are empty and a weight W2 when the storing parts 31a to 31c are filled with the concentrated reagent, from the memory (not shown) of the controller 23. Note that the weight W1 when the storing parts 31a to 31c are empty and the weight W2 when the storing parts 31a to 31c are filled with the concentrated reagent may be stored in the RAM 101c (see FIG. 5) of the server main body part 101 (see FIG. 1 and FIG. 2) of the server 100. Then, in step S42, the controller 23 acquires the weight data W transmitted from the weight sensors 32a to 32c (see FIG. 3) on which the storing parts 31a to 31c storing the concentrated reagent are placed.

Then, in step S43, the controller 23 detects a remaining amount R of the concentrated reagent, based on the weight data W thus acquired. Specifically, by substituting the weights W1 and the W2 read in step S41 and the weight data W acquired in step S42, for the following formula (1), the remaining amount R of the concentrated reagent is calculated. Then, in step S44, the remaining amount R of the concentrated reagent (concentrated reagent remaining amount data) thus calculated is transmitted to the server 100. Thereafter, when this concentrated reagent remaining amount data is transmitted to the client computer 200 (see FIG. 1) from the server 100, the remaining amount of the concentrated reagent is reflected on the remaining amount display part 411b and the remaining amount value column 433 displayed in the apparatus state screen 400a (see FIG. 7) and the preparation apparatus state detailed screen 400b (see FIG. 8). In this way, the remaining amount of the concentrated reagent stored in the storing parts 31a to 31c is acquired.

$$R=(W-W1)/(W2-W1) \quad (1)$$

Figure 16:
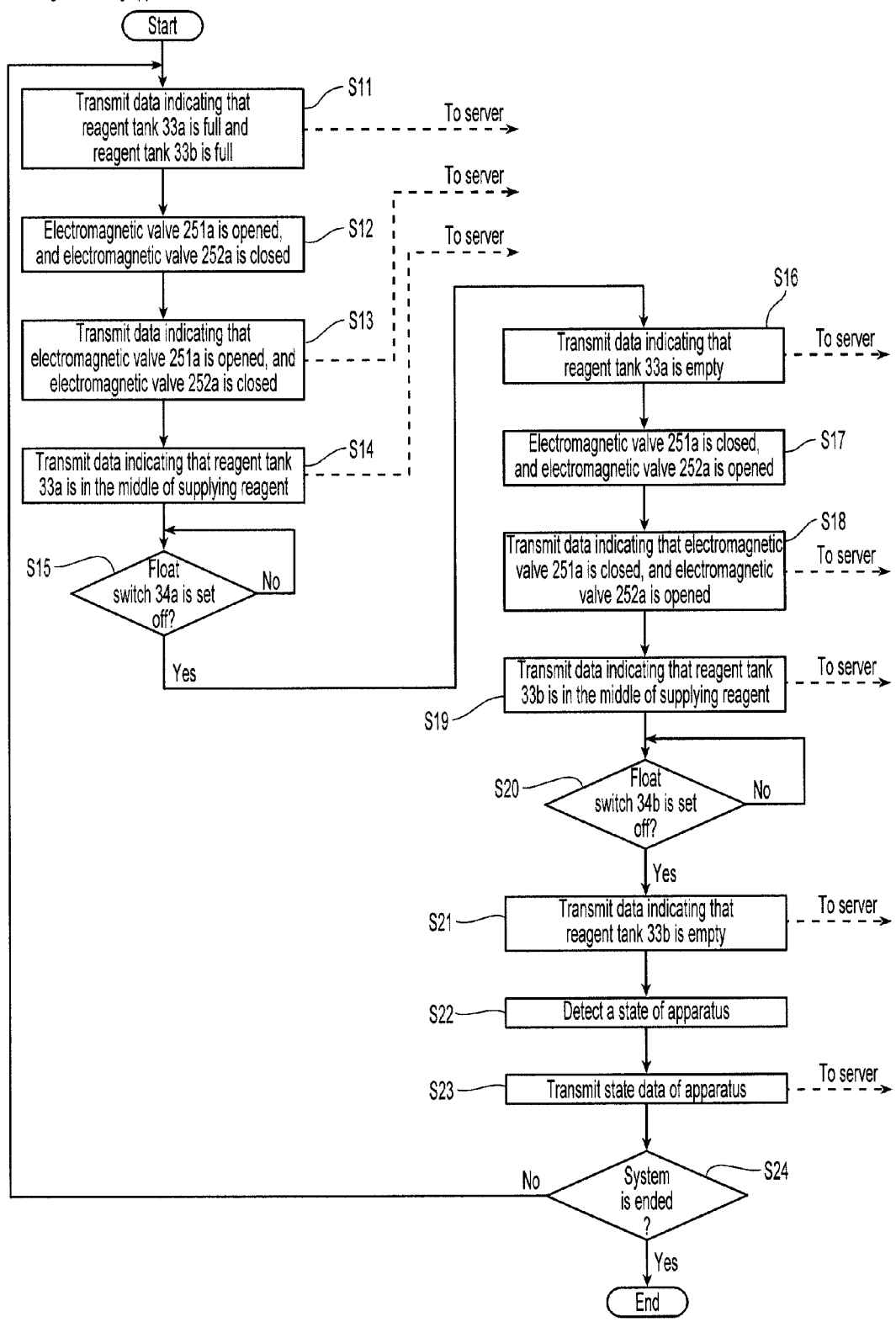
FIG. 16 is a flowchart showing the operation flow of the reagent feeding apparatus in the analyzing system according to one embodiment as shown in FIG. 1.

FIG. 16 is a flowchart showing an operation flow of the reagent feeding apparatus of the analyzing system according to one embodiment shown in FIG. 1. Next, the operation of the reagent feeding apparatus 30 of the analyzing system 1 according to one embodiment of the present invention will be explained, with reference to FIG. 1, FIG. 2, FIG. 4, FIG. 7, FIG. 9, and FIG. 16. Note that here, an explanation is given to a case of supplying the hemolytic agent stored in the reagent tanks 33a and the 33b (see FIG. 4), and the explanation for the operation of supplying the hemolytic agent stored in the reagent tanks 33c to 33j is omitted.

First, the reagent tank 33a (see FIG. 4) and the reagent tank 33b (see FIG. 4) filled with the same hemolytic agent (hemolytic agent A) are prepared. Then, the reagent tank 33a is connected to a portion on the electromagnetic valve 251a (see FIG. 4) side of the switching valve 25a, and the reagent tank 33b is connected to a portion on the electromagnetic valve 252a side of the switching valve 25a. Then, in step S11, the controller 26 transmits to the server 100 the data (hemolytic agent remaining amount data) indicating that the reagent tank 33a and the reagent tank 33b are filled with the hemolytic agent. Thereafter, when this hemolytic agent remaining amount data is transmitted to the client computer 200 (see FIG. 1) from the server 100, "full" is displayed in the apparatus state screen 400a (see FIG. 7) and the remaining amount presence/absence display column 421c of the reagent feeding apparatus information display part 420 of the reagent feeding apparatus state detailed screen 400c (see FIG. 9), and also "full" is displayed in the tank 1 column 443 and the tank 2 column 444 of the reagent feeding apparatus state detailed part 440 of the reagent feeding apparatus state detailed screen 400c.

Then, in step S12, the controller 26 opens the electromagnetic valve 251a for opening and closing the flow passage through which the hemolytic agent sent out from the reagent tank 33a flows, and closes the electromagnetic valve 252a for opening and closing the flow passage through which the hemolytic agent sent out from the reagent tank 33b flows. Thus, the hemolytic agent stored in the reagent tank 33a is supplied to the hematocyte counting apparatuses 3 by the switching valve 25a. Then, in step S13, the controller 26 transmits to the server 100 the data (electromagnetic valve switching data) indicating that the electromagnetic valve 251a opens and the electromagnetic valve 252a closes.

Then, in step S14, the controller 26 transmits to the server 100 the data (apparatus state data) indicating that the hemolytic agent stored in the reagent tank 33a is being supplied to the hematocyte counting apparatuses 3. Thereafter, when the hemolytic agent remaining amount data is transmitted from the server 100 to the client computer 200 (see FIG. 1), "full" is switched to "supply", which is displayed in a place corresponding to the reagent tank 33a of the remaining amount presence/absence display column 421c of the reagent feeding apparatus information display part 420, and also "full" is switched to "supply", which is displayed in the tank 1 column 443 corresponding to the reagent tank 33a of the reagent feeding apparatus state detailed part 440.

Thereafter, in step S15, the hemolytic agent in the reagent tank 33a is supplied to the hematocyte counting apparatuses 3, until the float switch 34a (see FIG. 4) disposed in the reagent tank 33a is set OFF. Then, in step S15, when the float switch 34a is set OFF, in step S16, the controller 26 transmits to the server 100 the data (hemolytic agent remaining amount data) indicating that the reagent tank 33a is empty. Thus, "supply" is switched to "empty", which is displayed in a place corresponding to the reagent tank 33a of the remaining amount presence/absence display column 421c of the reagent feeding apparatus information display part 420, and also "supply" is switched to "empty", which is displayed in the tank 1 column 443 corresponding to the reagent tank 33a of the reagent feeding apparatus state detailed part 440.

Then, in step S17, the electromagnetic valve 251a for opening and closing the flow passage closes, through which the hemolytic agent sent out from the reagent tank 33a flows, and also the electromagnetic valve 252a for opening and closing the flow passage opens, through which the hemolytic agent sent out from the reagent tank 33b flows. Thus, the hemolytic agent stored in the reagent tank 33b is supplied to the hematocyte counting apparatuses 3 by the switching valve 25a. Then, in step S18, the controller 26 transmits to the server 100 the data (electromagnetic switching data) indicating that the electromagnetic valve 252a opens and the electromagnetic valve 251a closes.

Then, in step S19, the controller 26 transmits to the server 100 the data (apparatus state data) indicating that the hemolytic agent stored in the reagent tank 33b is being supplied to the hematocyte counting apparatuses 3. Thereafter, when the hemolytic agent remaining amount data is transmitted to the client computer 200 (see FIG. 1), "full" is switched to "supply", which is displayed in a place corresponding to the reagent tank 33b of the remaining amount presence/absence display column 421c of the reagent feeding apparatus information display part 420, and also "full" is switched to "supply", which is displayed in the tank 2 column 444 corresponding to the reagent tank 33b of the reagent feeding apparatus state detailed part 440.

Thereafter, in step S20, the hemolytic agent in the reagent tank 33b is supplied to the hematocyte counting apparatuses 3, until the float switch 34b (see FIG. 4) disposed in the reagent tank 33b is set OFF. Then, in step S20, when the float switch 34b is set OFF, in step S21, the controller 26 transmits to the server 100 the data (hemolytic agent remaining amount data) indicating that the reagent tank 33b is empty. Thereafter, when this hemolytic agent remaining amount data is transmitted to the client computer 200 (see FIG. 1) from the server 100, "supply" is switched to "empty", which is displayed in a place corresponding to the reagent tank 33b of the remaining amount presence/absence display column 421c of the reagent feeding apparatus information display part 420, and also "supply" is switched to "empty", which is displayed in the tank 2 column 444 corresponding to the reagent tank 33b of the reagent feeding apparatus state detailed part 440.

Thereafter, in step S22, the state of the reagent feeding apparatus 30 (in the middle of operating or during shutdown of the apparatus) is detected, and in step S23, the state detected in step S22 is transmitted to the server 100 (see FIG. 1 and FIG. 2), as apparatus state data. Then, in step S24, the operations of the aforementioned steps S11 to step S23 are repeated, until the operation of the analyzing system 1 is determined to end. In this way, the operation of the reagent feeding apparatus 30 is controlled.

Figure 17:
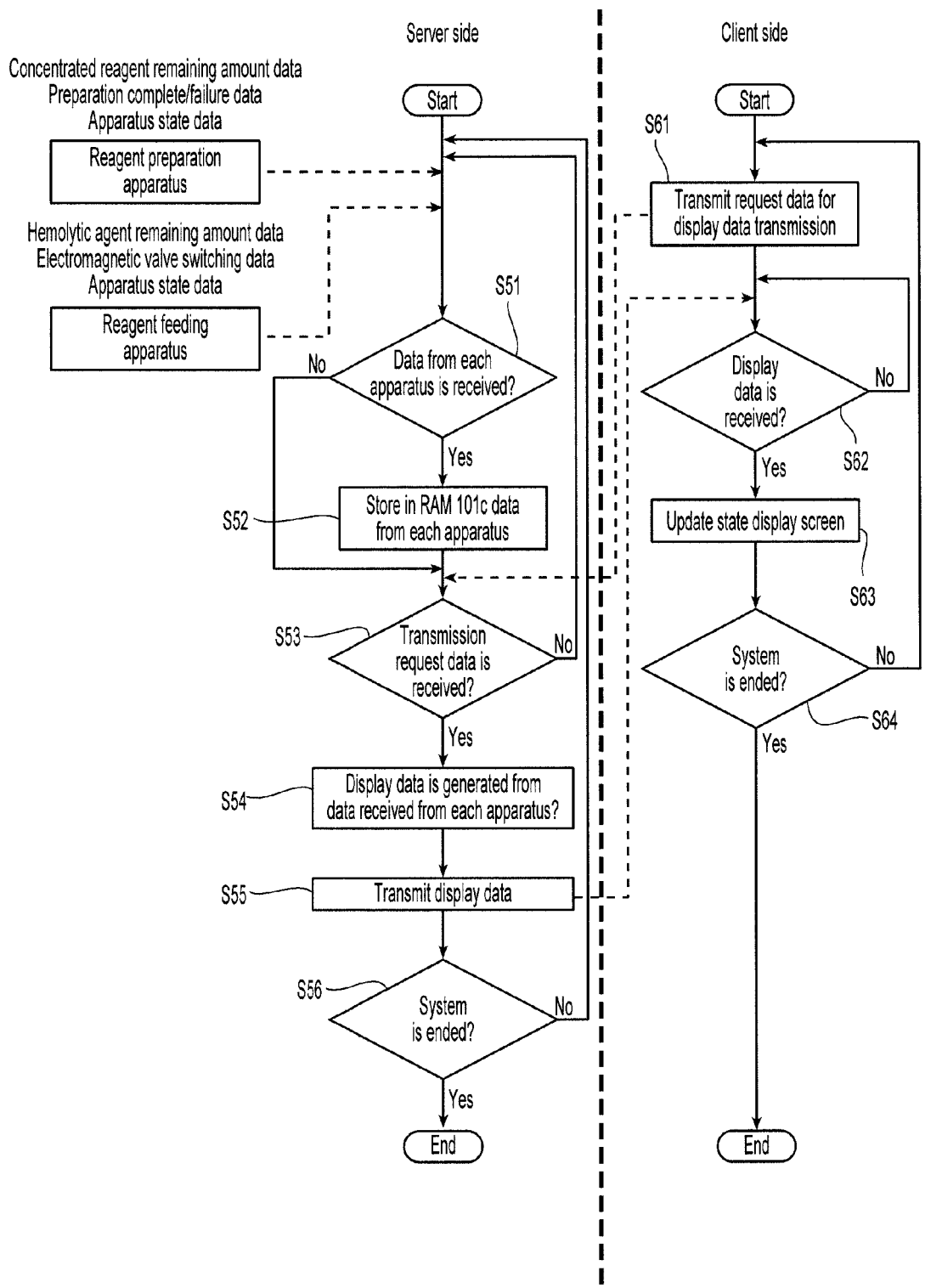
FIG. 17 is a flowchart showing an exchange between a sever and a client in the analyzing system according to one embodiment as shown in FIG. 1.

FIG. 17 is a flowchart showing an exchange of data between a sever and a client in the analyzing system according to one embodiment as shown in FIG. 1. Next, the exchange of data between the server 100 and the client computer 200 is explained, with reference to FIG. 1, FIG. 2, FIG. 7 to FIG. 12, and FIG. 17. The user operates the input part 203 of the client computer 200, and gives an instruction to start an application program of the Web browser. The CPU 201a receives this instruction, and loads the application program of the Web browser into the RAM 201c.

First, on the side of the server 100 (see FIG. 1 and FIG. 2), in step S51, the CPU 101a of the server 100 determines whether or not each kind of data transmitted from nine reagent preparation apparatuses 10 (see FIG. 2) and eight reagent feeding apparatuses 30 (see FIG. 2) is received. Specifically, it is determined whether or not the apparatus state data (step S8 of FIG. 13), preparation complete data (step S35 of FIG. 14), preparation failure data (step S36 of FIG. 14), and concentrated reagent remaining amount data (step S44 of FIG. 15) of the reagent preparation apparatus 10 transmitted from the reagent preparation apparatus 10, and the apparatus state data (step S14, step S19, and step S23 of FIG. 16), electromagnetic valve switching data (step S13 and step S18 of FIG. 16), and hemolytic agent remaining amount data (step S11, step S16, and step S21 of FIG. 16) of the reagent feeding apparatus 30 transmitted from the reagent feeding apparatus 30 are received.

Then, in step S51, when the CPU 101a determined that each kind of data from each apparatus (the reagent preparation apparatus 10 and the reagent feeding apparatus 30) is received, in step S52, the CPU 101a stores each kind of data thus received in the RAM 101c (see FIG. 5) of the server main body part 101. Then, in step S51, when the CPU 101a determined that each kind of data from each apparatus is not received, and in step S52, when each kind of data transmitted from each apparatus is stored in the RAM 101c of the server main body part 101, in step S53, the CPU 101a determines whether or not transmission request data transmitted from the client computer 200 (see FIG. 1) is received. Then, in step S53, when it is so determined that the transmission request data is not received, the aforementioned processing of step S51 and step S52 is repeated, until the transmission request data is received.

Then, in step S53, when the transmission request data is received, in step S54, display data is generated by using each kind of data stored in the RAM 101c of the server main body part 101. This display data is HTML (Hyper Text Markup. Language) data, being the data that can be browsed by using the Web browser installed on the client computer 200. Then, in step S55, the CPU 101a transmits the display data thus generated to the client computer 200 through the communication network 300 (see FIG. 1). Thereafter, in step S56, the aforementioned processing of step S51 to step S55 is repeated, until the analyzing system 1 is ended. In this way, the processing on the side of the server 100 is completed.

Meanwhile, on the side of the client computer 200, in step S61, the CPU 201a of the client computer 200 transmits the transmission request data to the server 100, so as to transmit the display data (HTML data) necessary in browsing by using the installed Web browser. Then, in step S62, the CPU 201a determines whether or not the display data transmitted from the server 100 is received. The processing of this step S62 is repeated until the display data is received. Then, in step S62, when it is so determined that the display data is received, in step S63, the display screen (see FIG. 7 to FIG. 12) displayed in the display part 202 of the client computer 200 is updated.

Thereafter, in step S64, by repeating the aforementioned processing of step S61 to step S63 until the analyzing system 1 is ended, the display screen (see FIG. 7 to FIG. 12) is successively updated by using the display data transmitted from the server 100. In this way, the processing of the client computer 200 is completed.

In this embodiment, as described above, the client computer 200 receives the display data generated by the server 100 and comprises the display part 202 for displaying the remaining amount of the reagent (concentrated reagent and the hemolytic agent) and the operation state (icons 411a and 421a) of the reagent preparation apparatus 10 and the reagent feeding apparatus 30 of each inspection line 1 to 9. Accordingly, the operator can confirm all of the remaining amount of the reagent used in each apparatus and the operation state thereof, in the display part 202 of the client computer 200. Therefore, it is not necessary for the operator to move to each apparatus to confirm the remaining amount of the reagent used in each apparatus of each inspection line 1 to 9 and the operation state thereof, thus making it possible to confirm the remaining amount of the reagent used in each apparatus and the operation state thereof without requiring labor and time. As a result, the operator can efficiently monitor the information regarding the remaining amount of the reagent used in each apparatus and the operation state thereof.

In addition, in this embodiment, the server 100 is connected to a plurality of reagent supplying apparatuses 2 and the client computer 200 through a communication network, receives the information regarding the remaining amount of the reagent and the information regarding the operation state of the plurality of reagent supplying apparatuses 2, and generates the display data. With this structure, the display data can be generated by the server 100 that receives the information regarding the remaining amount of the reagent and the information indicating the operation state of the plurality of reagent supplying apparatuses 2. As a result, each kind of information thus received can be processed by the server 100, and therefore the display data can be efficiently generated.

Also, in this embodiment, the reagent feeding apparatus 30 includes a plurality of reagent tanks (33a to 33j), switching valves (25a to 25e) for switching the reagent tanks as supply sources of the reagent, and the controller 26 for controlling the operation of the switching valve so as to switch the reagent tanks as the supply sources of the reagent, based on the remaining amount of the reagent thus acquired. With this structure, when the reagent stored in one of the reagent tanks is empty, the reagent tanks can be switched so that the reagent can be supplied from the other reagent tank. As a result, even if the reagent of one of the reagent tanks is empty, the reagent can be continuously supplied to the hematocyte counting apparatuses 3 from the other reagent tank.

In addition, in this embodiment, by providing in the reagent preparation apparatus 10, the electric conductivity meter 18 for detecting the electric conductivity of the diluted solution stored in the dilution part 16, the electric conductivity of the diluted solution supplied to the hematocyte counting apparatuses 3 and the blood sample smearing apparatus 4 can be monitored. Thus, variation of the electric conductivity of the diluted solution supplied to the hematocyte counting apparatuses 3, etc., can be prevented. As a result, the hematocyte counting apparatuses 3, etc can analyze by using the diluted solution with substantially constant electric conductivity, and therefore an accurate analysis result can be obtained.

The embodiment disclosed herein is in all aspects simply an example and not to be considered limiting in any way. The scope of the present invention is defined in the scope of the claims and not by the description of the embodiment, and further includes all modifications, meanings and equivalences that fall within the scope of the claims.

For example, in the example of the embodiment described above, the controller of the reagent preparation apparatus calculates the remaining amount of the concentrated reagent, based on the weight data transmitted from the weight sensor. However, the present invention is not limited thereto, and the processing of calculating the remaining amount of the concentrated reagent may be performed by the main body of the server or may be performed by the main body of the client.

Also, in the example of the embodiment described above, the remaining amount of the concentrated reagent is calculated based on the weight data transmitted from the weight sensor. However, the present invention is not limited thereto, and the concentrated reagent may be calculated based on a liquid level detected by a sensor, which is provided for detecting the liquid level of the reagent. As the aforementioned sensor, an electrical sensor for detecting a contact between a reagent sampling nozzle and a liquid surface by a change of an electrostatic capacitance and an electrical resistance, and an optical sensor for optically monitoring the liquid level can be applied.

In addition, in the example of the embodiment described above, the display data is generated on the side of the server by using each kind of data transmitted to the main body part of the server. However, the present invention is not limited thereto, and each kind of data transmitted from each apparatus (the reagent preparation apparatus and the reagent feeding apparatus) may be received by the client without providing the server, and the display data may be generated on the side of the client by using the data thus received. With this structure, integrated information can be generated by a monitoring apparatus, without providing the computer such as a server for generating the integrated information integrating the remaining amount of the reagent and the operation state of each reagent supplying apparatus.

Further, in the example of the embodiment described above, the display data is displayed on the display screen of the display part 202 of the client computer 200. However, the display data may be displayed to the operator by printing this display data on a paper.

Also, in the example of the embodiment described above, presence/absence of the hemolytic agent stored in the reagent tank is detected by the float switch. However, the present invention is not limited thereto, and instead of providing the float switch, the reagent tank storing the hemolytic agent may be placed on the weight sensor. Thus, not only the presence/absence of the hemolytic agent, but also the remaining amount of the hemolytic agent can be acquired.

In addition, in the apparatus state screen (see FIG. 7) of the example of the aforementioned embodiment, the mark "☐" is displayed to request the exchange of the reagent. However, the present invention is not limited thereto, and in addition to this mark "☐", "exchange" may be displayed to further urge the operator to exchange the reagent.

Also, in the example of the embodiment described above, three sets of pure water quantity measuring tank, pure water quantity measuring pump, reagent quantity measuring tank, concentrated reagent quantity measuring pump, dilution part, stirring part, electric conductivity meter, reagent storage tank, circulation pump, filter, and reagent supplying tank are provided so as to correspond to three storing parts. However, the present invention is not limited thereto, and the switching part (such as a switching valve) for switching three storing parts may be provided in the reagent preparation apparatus, and also one set of the aforementioned each part may be provided. In this case, although blending of concentrated reagents occurs for each storing part in the reagent preparation apparatus, when the same kind of concentrated reagent is used, the constitution of the reagent preparation apparatus can be simplified.

What is claimed:

1. An analyzing system, comprising:
    a plurality of inspection lines, each comprising:
        a reagent supplying apparatus, and
        a plurality of hematology analyzers, each configured to analyze a measurement sample prepared from a blood sample and a reagent supplied from the reagent supplying apparatus, and count the number of red blood cells in the blood sample; and
    a computer connected to the plurality of reagent supplying apparatuses via a communication network,
    wherein each reagent supplying apparatus comprises a storing part configured to store a concentrated reagent, a detector configured to detect a weight of the storing part or liquid level in the storing part, a first controller configured to calculate a remaining amount data reflecting a remaining amount of the concentrated reagent from an output of the detector and to transmit the calculated remaining amount data to the computer,
    wherein each reagent supplying apparatus supplies the reagent to the plurality of hematology analyzers, and
    wherein the computer comprises a display, and a second controller configured to receive the plurality of remaining amount data transmitted from the plurality of reagent supplying apparatuses via the communication network, to generate a display data integrating the plurality of received remaining amount data and to show the generated display data on the display.

2. The analyzing system of claim 1, wherein
    the computer includes a server computer and a client computer;
    the server computer is configured to receive the plurality of remaining amount data transmitted from the plurality of reagent supplying apparatuses via the communication network, and generate the display data; and the client computer is communicatively connected to the server computer and comprises the display.

3. The analyzing system of claim 1, wherein the reagent supplying apparatus further comprises a preparation part configured to prepare the reagent from the concentrated reagent;

the first controller of the reagent supplying apparatus is configured to acquire a preparation state information indicating a preparation state of the reagent prepared by the preparation part, and to transmit the acquired preparation state information to the computer; and the second controller of the computer is configured to receive the plurality of preparation state information transmitted from the plurality of reagent supplying apparatuses, and to generate the display data further integrating the plurality of received preparation state information.

4. The analyzing system of claim 3, wherein the reagent supplying apparatus further comprises a concentration detector configured to detect a concentration of a specific substance in a liquid in the preparation part, and the first controller of the reagent supplying apparatus is configured to acquire the preparation state information, based on the concentrated detected by the concentration detector.

5. The analyzing system of claim 2, wherein the plurality of inspection lines and the server computer are provided in a sample processing center; and the client computer is provided on a place separated from the sample processing center.

6. The analyzing system of claim 1, wherein the first controller of the reagent supplying apparatus is configured to further transmit an operation state information indicating an operation state of the reagent supplying apparatus to the computer;

the second controller of the computer is configured to receive the plurality of operation state information transmitted from the plurality of reagent supplying apparatuses, and to generate the display data further integrating the plurality of received operation state information.

7. The analyzing system of claim 1, wherein the inspection line comprises a conveying apparatus configured to convey blood samples to each hematology analyzer.

* * * * *